United States Patent
Pozniak et al.

(12)

(10) Patent No.: US 6,579,275 B1
(45) Date of Patent: Jun. 17, 2003

(54) PANT-LIKE DISPOSABLE ABSORBENT ARTICLES WITH RELEASABLE SEAMS AND A FOLDED FASTENING FEATURE

(75) Inventors: Jennifer Elizabeth Pozniak, Appleton, WI (US); Cassandra Elizabeth Morris, Charlottesville, VA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 168 days.

(21) Appl. No.: 09/675,544

(22) Filed: Sep. 28, 2000

(51) Int. Cl.$^7$ ................................................ A61F 13/15
(52) U.S. Cl. .................. 604/390; 604/389; 604/385.11; 604/385.05; 604/391; 604/385.01; 604/385.3; 604/385.29; 604/385.25; 604/385.23
(58) Field of Search ............................ 604/385.01, 358, 604/391, 396, 385.03, 385.11, 389

(56) References Cited

U.S. PATENT DOCUMENTS

| | | | |
|---|---|---|---|
| 1,079,479 A | 11/1913 | Earnshaw | |
| 1,485,001 A | 2/1924 | Wills | |
| 1,657,909 A | 1/1928 | Abramovich | |
| 1,705,194 A | 3/1929 | Marinsky | |
| 1,762,468 A | 6/1930 | Brewer | |
| 1,963,334 A | 6/1934 | Neilson | |
| 2,201,255 A | 5/1940 | Wilson, Jr. | |

(List continued on next page.)

FOREIGN PATENT DOCUMENTS

| | | |
|---|---|---|
| AU | 667899 | 4/1996 |
| CA | 2096672 | 11/1993 |
| CA | 2103992 A1 | 2/1994 |

(List continued on next page.)

OTHER PUBLICATIONS

Derwent World Patent Database abstract of FR 2762507 A1: Description of Rahala, "Baby's Disposable Nappy."

Derwent World Patent Database abstract of JP 6–063076 A: Description of Kao Corp. (Kaos), "Throw Away Diaper Or Nappy."

Derwent World Patent Database abstract of JP 95–044941 B2: Description of Zuiko KK (ZUIK–N), "Simple Solid Diaper For Eliminating Waste of Material by Using Square Shape."

(List continued on next page.)

*Primary Examiner*—John J. Calvert
*Assistant Examiner*—Angela J. Grayson
(74) *Attorney, Agent, or Firm*—Jeffrey B Curtin; Alyssa A. Dudkowski

(57) ABSTRACT

A pant-like, disposable absorbent article includes an absorbent chassis, a pair of opposed side panels, at least one releasable joint and at least one folded fastenery. The absorbent chassis defines a pair of laterally opposed side edges and a pair of longitudinally opposed waist edges. The side panels extend between the side edges of the absorbent chassis to define a waist opening and a pair of leg openings in the pant-like disposable absorbent article. Each of the opposed side panels defines a first side margin which is permanently attached to the side edge of the absorbent chassis in one waist region of the absorbent article to provide a permanent joint. At least one of the opposed side panels further defines a second side margin opposite the first side margin which is releasably attached to the side edge of the absorbent chassis in the other waist region of the absorbent article to provide a releasable joint. The folded fastener is located adjacent the releasable joint wherein the folded fastener is configured to be unfolded and used to refastenably engage the second side margin of the at least one side panel to the opposite waist region of the absorbent article after the releasable joint is released.

60 Claims, 9 Drawing Sheets

U.S. PATENT DOCUMENTS

| | | |
|---|---|---|
| 2,242,977 A | 5/1941 | Marcos |
| 2,475,175 A | 7/1949 | Cadous |
| 2,477,914 A | 8/1949 | Webb |
| 2,545,761 A | 3/1951 | Brink |
| 2,570,963 A | 10/1951 | Mesmer |
| 2,630,120 A | 3/1953 | Nielson |
| 2,630,806 A | 3/1953 | Kiscaden |
| 2,743,725 A | 5/1956 | Matthews |
| 2,801,632 A | 8/1957 | Burner et al. |
| 2,808,831 A | 10/1957 | Winslett |
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Sr. |
| 3,638,651 A | 2/1972 | Torr |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A | 5/1988 | Cole |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A | 12/1991 | Davis |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A | 1/1993 | Roessler et al. |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A | 12/1994 | Ando et al. |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |
| 5,489,282 A | 2/1996 | Zehner et al. |
| 5,496,298 A | 3/1996 | Kuepper et al. |
| 5,499,978 A | 3/1996 | Buell et al. |
| 5,500,063 A | 3/1996 | Jessup |
| 5,509,915 A | 4/1996 | Hanson et al. |
| 5,527,302 A | 6/1996 | Endres et al. |

| | | |
|---|---|---|
| H1558 H | 7/1996 | Goulait et al. |
| 5,531,731 A | 7/1996 | Brusky |
| 5,531,732 A | 7/1996 | Wood |
| 5,537,722 A | 7/1996 | Niederhofer et al. |
| 5,540,796 A | 7/1996 | Fries |
| 5,545,158 A | 8/1996 | Jessup |
| 5,545,275 A | 8/1996 | Herrin et al. |
| 5,549,592 A | 8/1996 | Fries et al. |
| 5,554,146 A | 9/1996 | Niederhofer et al. |
| 5,562,650 A | 10/1996 | Everett et al. |
| 5,569,232 A | 10/1996 | Roe et al. |
| 5,569,234 A | 10/1996 | Buell et al. |
| 5,571,586 A | 11/1996 | Gobran |
| 5,575,784 A | 11/1996 | Ames-Ooten et al. |
| 5,582,606 A | 12/1996 | Bruemmer et al. |
| 5,591,152 A | 1/1997 | Buell et al. |
| 5,593,401 A | 1/1997 | Sosalla et al. |
| 5,601,546 A | 2/1997 | Tanji et al. |
| 5,605,735 A | 2/1997 | Zehner et al. |
| 5,607,416 A | 3/1997 | Yamamoto et al. |
| 5,611,789 A | 3/1997 | Seth |
| 5,618,366 A | 4/1997 | Suekane |
| 5,624,420 A | 4/1997 | Bridges et al. |
| 5,624,424 A | 4/1997 | Saisaka et al. |
| 5,624,428 A | 4/1997 | Sauer |
| 5,624,429 A | 4/1997 | Long et al. |
| 5,626,574 A | 5/1997 | Sasaki et al. |
| 5,628,738 A | 5/1997 | Suekane |
| 5,629,063 A | 5/1997 | Gobran |
| 5,634,916 A | 6/1997 | Lavon et al. |
| H1674 H | 8/1997 | Ames et al. |
| 5,656,111 A | 8/1997 | Dilnik et al. |
| 5,662,637 A | 9/1997 | Kitaoka et al. |
| 5,662,638 A | 9/1997 | Johnson et al. |
| 5,665,084 A | 9/1997 | Richmond |
| 5,669,897 A | 9/1997 | Lavon et al. |
| 5,685,873 A | 11/1997 | Bruemmer |
| 5,685,874 A | 11/1997 | Buell et al. |
| 5,690,626 A | 11/1997 | Suzuki et al. |
| 5,690,627 A | 11/1997 | Clear et al. |
| 5,693,038 A | 12/1997 | Suzuki et al. |
| 5,695,488 A | 12/1997 | Sosalla |
| 5,695,868 A | 12/1997 | McCormack |
| D389,320 S | 1/1998 | Vinnage et al. |
| 5,707,364 A | 1/1998 | Coates |
| 5,711,832 A | 1/1998 | Glaug et al. |
| 5,725,518 A | 3/1998 | Coates |
| 5,759,317 A | 6/1998 | Justmann |
| 5,772,649 A | 6/1998 | Siudzinski |
| 5,772,825 A | 6/1998 | Schmitz |
| 5,788,685 A | 8/1998 | Ronnberg et al. |
| 5,788,797 A | 8/1998 | Herrin et al. |
| 5,795,433 A | 8/1998 | Niedermeyer |
| 5,827,259 A | 10/1998 | Laux et al. |
| 5,827,260 A | 10/1998 | Suzuki et al. |
| 5,830,206 A | 11/1998 | Larsson |
| 5,843,056 A | 12/1998 | Good et al. |
| 5,855,574 A | 1/1999 | Kling et al. |
| 5,876,531 A | 3/1999 | Jacobs et al. |
| 5,897,545 A | 4/1999 | Kline et al. |
| 5,899,896 A | 5/1999 | Suprise et al. |
| 5,904,673 A | 5/1999 | Roe et al. |
| 5,904,802 A | 5/1999 | Niedermeyer |
| 5,916,203 A | 6/1999 | Brandon et al. |
| 5,916,207 A | 6/1999 | Toyoda et al. |
| 5,919,334 A | 7/1999 | Niedermeyer |
| 5,938,652 A | 8/1999 | Sauer |
| 5,944,707 A | 8/1999 | Ronn |
| 5,961,761 A | 10/1999 | Heindel et al. |
| 5,971,153 A | 10/1999 | Bauer et al. |
| 6,022,430 A | 2/2000 | Blenke et al. |
| 6,022,431 A | 2/2000 | Blenke et al. |
| 6,022,432 A | 2/2000 | Elsberg et al. |
| 6,030,373 A | 2/2000 | VanGompel et al. |
| 6,036,805 A | 3/2000 | McNichols |
| 6,045,543 A | 4/2000 | Pozniak et al. |
| 6,113,717 A * | 9/2000 | Vogt et al. .................. 156/227 |
| 6,149,638 A | 11/2000 | Vogt et al. |
| 6,287,287 B1 | 9/2001 | Elsberg |
| 6,322,552 B1 | 11/2001 | Blenke et al. |
| 6,336,922 B1 | 1/2002 | VanGompel et al. |
| 6,361,527 B1 | 3/2002 | VanGompel et al. |

FOREIGN PATENT DOCUMENTS

| | | |
|---|---|---|
| CA | 2187021 A1 | 10/1995 |
| CA | 2187366 A1 | 10/1995 |
| EP | 0 206 208 B1 | 12/1986 |
| EP | 0 217 032 A2 | 4/1987 |
| EP | 0 251 251 A3 | 1/1988 |
| EP | 0 463 276 A1 | 1/1992 |
| EP | 0 532 034 A2 | 3/1993 |
| EP | 0 544 703 B1 | 6/1993 |
| EP | 0 696 911 B1 | 2/1996 |
| EP | 0 753 292 A2 | 1/1997 |
| EP | 0 487 758 B1 | 3/1997 |
| EP | 0 597 331 B1 | 11/1997 |
| EP | 0 809 992 A1 | 12/1997 |
| EP | 0 878 180 A2 | 11/1998 |
| FR | 2566631 | 1/1986 |
| GB | 1 520 740 | 8/1978 |
| GB | 2 244 422 B | 12/1991 |
| GB | 2 267 024 B | 11/1993 |
| GB | 2 288 314 A | 10/1995 |
| GB | 2 288 315 A | 10/1995 |
| GB | 2 288 316 A | 10/1995 |
| GB | 2 291 783 A | 2/1996 |
| GB | 2 294 867 A | 5/1996 |
| GB | 2 297 473 A | 6/1996 |
| GB | 2 308 290 A | 6/1997 |
| JP | 6-77718 U | 11/1994 |
| JP | 7-213553 A | 8/1995 |
| JP | 7- 227407 A | 8/1995 |
| JP | 7-255773 A | 10/1995 |
| JP | 7-299094 A | 11/1995 |
| JP | 8-229072 A | 9/1996 |
| JP | 9-287 U | 5/1997 |
| JP | 11-47188 A | 2/1999 |
| WO | WO 83/04163 A1 | 12/1983 |
| WO | WO 90/07313 A1 | 7/1990 |
| WO | WO 91/04724 A1 | 4/1991 |
| WO | WO 91/08725 A1 | 6/1991 |
| WO | WO 92/22274 A1 | 12/1992 |
| WO | WO 93/09742 A1 | 5/1993 |
| WO | WO 94/17768 A1 | 8/1994 |
| WO | WO 95/01148 A1 | 1/1995 |
| WO | WO 95/02383 A1 | 1/1995 |
| WO | WO 95/13772 A1 | 5/1995 |
| WO | WO 95/22951 A1 | 8/1995 |
| WO | WO 95/27460 A1 | 10/1995 |
| WO | WO 95/27462 A1 | 10/1995 |
| WO | WO 95/29657 A1 | 11/1995 |
| WO | WO 96/03101 A1 | 2/1996 |
| WO | WO 96/18315 A1 | 6/1996 |
| WO | WO 96/29037 A1 | 9/1996 |
| WO | WO 96/32084 A1 | 10/1996 |
| WO | WO 97/15260 A1 | 5/1997 |
| WO | WO 97/23186 A1 | 7/1997 |
| WO | WO 97/25951 A1 | 7/1997 |
| WO | WO 97/31605 A1 | 9/1997 |
| WO | WO 97/32555 A1 | 9/1997 |
| WO | WO 97/33547 A1 | 9/1997 |
| WO | WO 97/46197 A1 | 12/1997 |

| | | |
|---|---|---|
| WO | WO 97/47265 A1 | 12/1997 |
| WO | WO 97/48357 A1 | 12/1997 |
| WO | WO 98/03140 A1 | 1/1998 |
| WO | WO 98/18421 A1 | 5/1998 |
| WO | WO 98/29251 A1 | 7/1998 |
| WO | WO 98/51252 A1 | 11/1998 |
| WO | WO 98/56328 A1 | 12/1998 |
| WO | WO 99/07319 A1 | 2/1999 |
| WO | WO 99/14045 A1 | 3/1999 |
| WO | WO 99/56688 A1 | 11/1999 |
| WO | WO 99/65438 A1 | 12/1999 |
| WO | WO 99/65442 A1 | 12/1999 |
| WO | WO 00/37009 A2 | 6/2000 |
| WO | WO 00/37010 A1 | 6/2000 |
| WO | WO 01/43682 A1 | 6/2001 |
| WO | WO 01/43683 A1 | 6/2001 |
| WO | WO 01/70155 A1 | 9/2001 |

OTHER PUBLICATIONS

Derwent World Patent Database abstract of JP 9–276334 A: Description of Kao Corp (Kaos), "Disposable Baby Nappy."

Derwent World Patent Database abstract of JP 11–070143 A: Description of Toyo Eisai KK (TOEI–N), "Disposable Diaper For Adults And Children."

Derwent World Patent Database abstract of JP 11–076299 A: Description of Uni–Charm KK (UNIC–N), "Disposable Diaper."

* cited by examiner

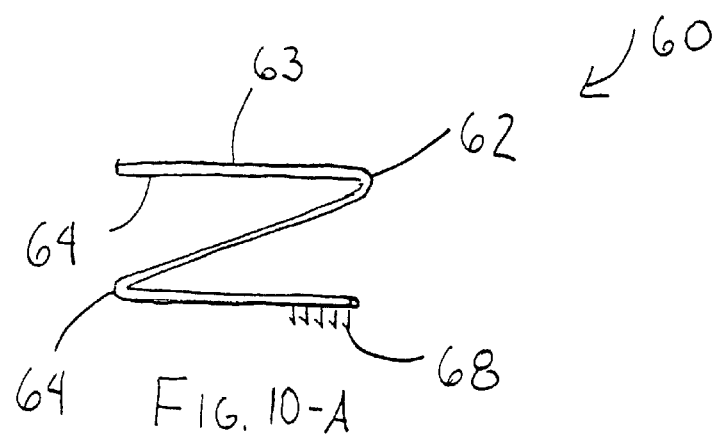
FIG. 10-A
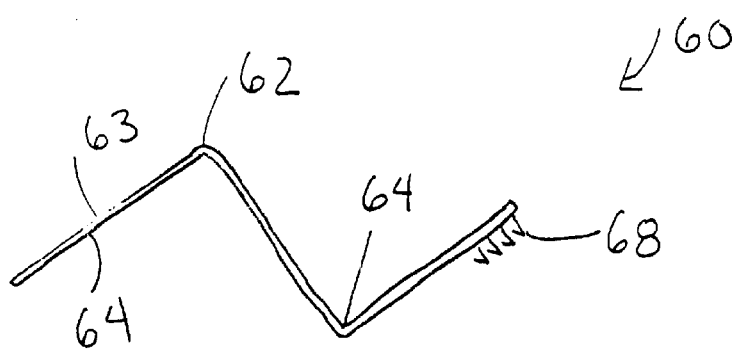
FIG. 10-B
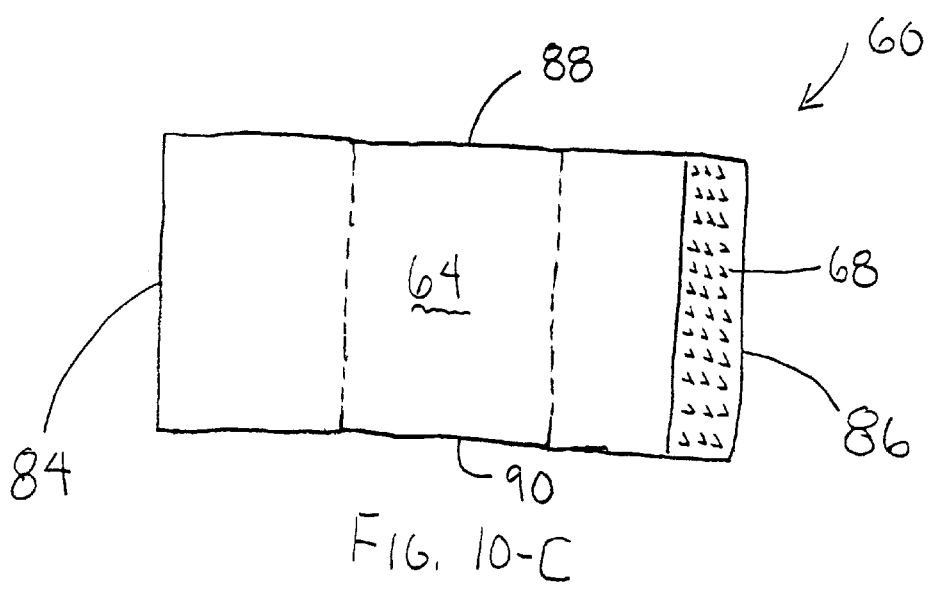
FIG. 10-C

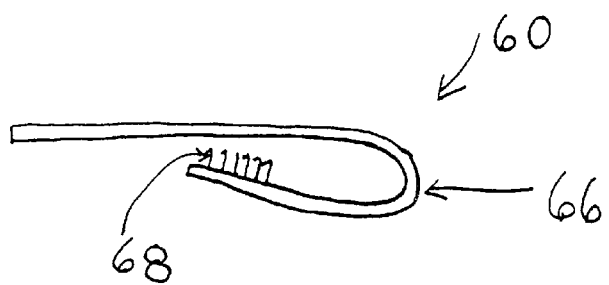
FIG. 11-A
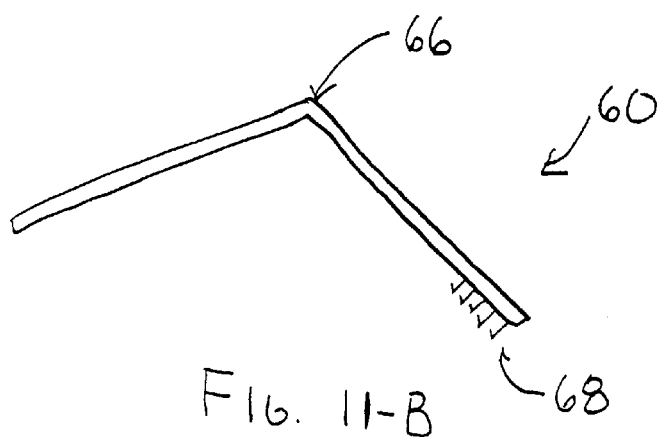
FIG. 11-B
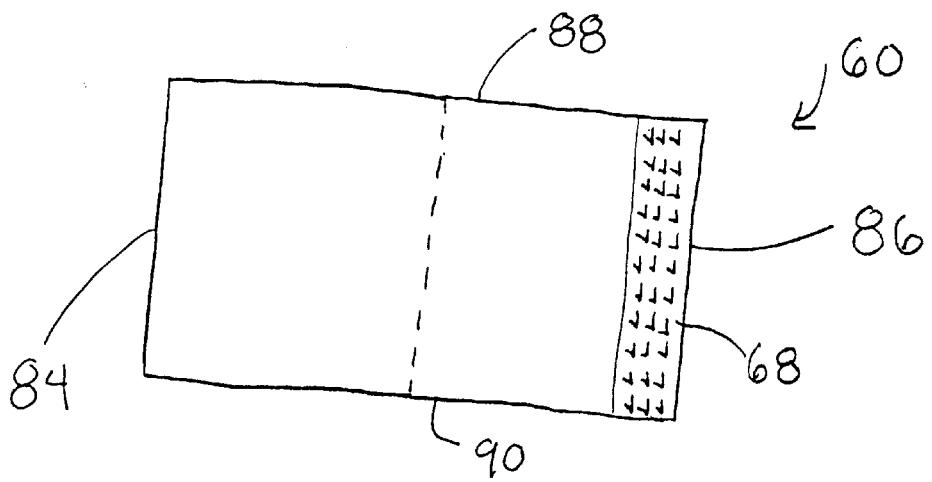
FIG. 11-C

PANT-LIKE DISPOSABLE ABSORBENT ARTICLES WITH RELEASABLE SEAMS AND A FOLDED FASTENING FEATURE

FIELD OF THE INVENTION

The present invention relates to disposable absorbent articles which are adapted to contain body exudates. More particularly, the present invention relates to pant-like disposable absorbent articles having releasable seams and a folded fastening feature.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the caregiver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. In such circumstances it is further desirable that the caregiver or the wearer may be able to apply the absorbent article to a wearer in a prone position similar to a conventional diaper. Such absorbent articles can assist in the toilet training of children.

Conventional diapers are not provided in a prefastened condition and have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the exterior surface of the outer cover of the diaper in the front waist portion of the diaper. In such a configuration, the diaper has been positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached. Moreover, the fasteners on such conventional diapers are typically exposed to the wearer and the surroundings during the diapering process. This may result in the inadvertent attachment of the fasteners with the diaper or with the wearer's clothing, further complicating the diapering process. In addition, the exposed fasteners may have the potential to irritate the wearer's skin.

Several attempts have been made to provide absorbent articles which effectively contain body exudates and are capable of being pulled up or down over the hips of the wearer. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to-be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer. Finally, some of these conventional training pants do not provide the option of being applied as a conventional diaper.

Accordingly, despite the attempts to develop improved absorbent articles, there remains a need for absorbent articles which can effectively provide the benefits of both conventional training pants and conventional diapers. That is, there remains a need for absorbent articles which conform to the wearer to effectively contain bodily exudates, which are capable of being pulled up and down over the hips and buttocks of the wearer without opening, which are readily secured about and removed from the wearer in a convenient and clean manner and which allow easy inspection by the care giver to assist in determining whether the article is soiled. Moreover, there is a need that such pant-like disposable absorbent articles are also capable of being applied in the manner of a conventional diaper, to a wearer lying in a prone position.

SUMMARY OF THE INVENTION

In response to the difficulties and problems discussed above, new pant-like disposable absorbent articles which have at least one releasable joint and at least one folded fastener have been discovered. In one aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article also includes a pair of opposed side panels which extend outward from and between the side edges of the absorbent chassis in the front waist region and back waist region of the absorbent article to define a waist opening and a pair of leg openings in the pant-like disposable absorbent article. At least one of the opposed side panels defines a first side margin which is permanently attached to the side edge of the absorbent chassis in one of the waist regions of the absorbent article to provide a permanent joint and a second side margin which is releasably attached to the side edge of the absorbent chassis in the opposite waist region of the absorbent article to provide a releasable joint. The absorbent article also includes a first folded fastener located adjacent the at least one releasable joint. The folded fastener is configured to be unfolded and used to refastenably engage the second side margin of the at least one side panel to the opposite waist region of the absorbent article after the releasable joint is released.

In another aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article also includes a pair of laterally opposed, extensible back panels which are permanently attached to the side edges of the absorbent chassis in the back waist region of the absorbent article, and a pair of laterally opposed, extensible front panels which are releasably attached to the side edges of the absorbent chassis in the front waist region of the absorbent article to provide a pair of releasable joints. The front and back panels on each side edge of the absorbent chassis are permanently connected together along a side seam to define a waist opening and a pair of leg openings. The absorbent article also includes a pair of folded fasteners located adjacent the releasable joints. The folded fasteners are held in a folded arrangement and are configured to be unfolded and used to refastenably attach the front panels to the front waist region of the absorbent article after the releasable joints are released.

In yet another aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges.

The absorbent article further includes a pair of laterally opposed, extensible back panels which are permanently attached to the side edges of the absorbent chassis in the back waist region of the absorbent chassis. Still further, the absorbent article includes a pair of laterally opposed, extensible front panels which are permanently attached to the side edges of the absorbent chassis in the front waist region of the absorbent article. The front panel and the back panel on each side edge of the absorbent chassis are refastenably connected together along a side seam to provide a pair of releasable joints and to define a waist opening and a pair of leg openings. The absorbent article also includes a pair of folded fasteners located adjacent the releasable joints. The folded fasteners are held in a folded arrangement and are configured to be unfolded and used to refastenably engage the back panels to the front waist region of the absorbent article after the releasable joints are released.

In still yet another aspect, the present invention concerns a pant-like, disposable absorbent article which defines a front waist region, a back waist region, a crotch region which extends between and connects the waist regions, a longitudinal direction and a lateral direction. The absorbent article includes an absorbent chassis which defines an absorbent core, an exterior surface, an interior surface opposite the exterior surface, a pair of laterally opposed side edges and a pair of longitudinally opposed waist edges. The absorbent article further includes a pair of laterally opposed, extensible back panels which are permanently attached to the side edges of the absorbent chassis in the back waist region of the absorbent chassis. Still further, the absorbent article includes a pair of laterally opposed, extensible front panels which are permanently attached to the side edges of the absorbent chassis in the front waist region of the absorbent article. The front panel and the back panel on each side edge of the absorbent chassis are refastenably connected together along a side seam to provide a pair of releasable joints and to define a waist opening and a pair of leg openings. The absorbent article also includes a pair of folded fasteners located adjacent the releasable joints. The folded fasteners define an inboard edge, and an outboard edge wherein the inboard edge defines a length in the longitudinal direction which is greater than a length of the outboard edge in the longitudinal direction. The folded fasteners are held in a folded arrangement and are configured to be unfolded and used to refastenably engage the back panels to the front waist region of the absorbent article after the releasable joints are released.

The present invention advantageously provides pant-like, disposable absorbent articles which include a releasable joint and a folded fastener. In particular, the present invention provides pant-like disposable absorbent articles which are capable of being reliably pulled up or down over the hips of the wearer to assist in the toilet training of the wearer similar to conventional training pants. Moreover, similar to conventional diapers, the pant-like disposable absorbent articles of the present invention can be advantageously applied to and removed from the wearer similar to conventional diapers. Further, the pant-like disposable absorbent articles of the present invention allow easy inspection by the caregiver to assist in determining whether the article is soiled similar to conventional diapers. As such, the present invention provides a dual use absorbent article which can function as both a pant-like absorbent article and as a conventional diaper. This dual use capability may be particularly desirable for use with active wearers. Still further, the pant-like disposable absorbent articles of the present invention provide a folded fastener which reduces exposure of the active fastening area of the fastener to the wearer and their clothing. Therefore, the opportunity for irritation of the wearer's skin is lowered, and the application of the article is eased as the opportunity for inadvertent snagging is diminished. Finally, the folded fastener may be configured to better conform to the area between the leg and torso of the wearer than the full-length seams provided by the article when it is in the pant-like configuration. Therefore, the use of the folded fastener of the present invention, upon disengagement of the releasable joint, can provide a closer, more conforming fit to the wearer, reduce the opportunity for leaks, and provide the wearer with greater flexibility and range of motion.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

FIG. 10-A representatively shows a top plan view of the folded fastener in the z-folded configuration;

FIG. 10-B representatively shows a top plan view of the folded fastener in the z-folded configuration wherein the z-fold fastener is partially extended;

FIG. 10-C representatively shows a front plan view of the folded fastener in the z-folded configuration;

FIG. 11-A representatively shows a top plan view of the folded fastener in the j-fold configuration;

FIG. 11-B representatively shows a top plan view of the folded fastener in the j-folded configuration wherein the j-fold fastener is partially extended; and FIG. 11-C representatively shows a front plan view of the folded fastener in the j-folded configuration.

DETAILED DESCRIPTION OF THE INVENTION

The present invention concerns pant-like, disposable absorbent articles which are adapted to be worn adjacent to the body of a wearer to absorb and contain various exudates discharged from the body. The pant-like absorbent articles are configured to closely conform to the body of the wearer to effectively contain body exudates while being capable of being pulled up or down over the hips and buttocks of the wearer. The absorbent articles also include at least one releasable joint and at least one folded fastener such that they can be secured to and removed directly from the waist of the wearer and easily inspected to determine if they have been soiled during use. As such, the pant-like, disposable absorbent articles of the present invention can function in a similar manner to conventional training pants when left in the pant-like configuration. Alternatively, the releasable joints may be disengaged and the folded fasteners opened up and exposed prior to or during use to allow the disposable absorbent articles of the present invention to be used similar to a conventional diaper. As used herein, the term "disposable" refers to articles which are intended to be discarded after a limited use and which are not intended to be laundered or otherwise restored for reuse.

The pant-like disposable absorbent articles of the present invention will be described in terms of a disposable, pant-like diaper article which is adapted to be worn by infants about the lower torso. In particular, the pant-like disposable absorbent articles will be described in terms of a pant-like, disposable diaper having side panels, at least one releasable joint and at least one folded fastener. It is understood that the articles and methods of the present invention are equally adaptable for other types of absorbent articles such as adult incontinent products, training pants, feminine hygiene products, other personal care or health care garments, and the like.

Figure 1:
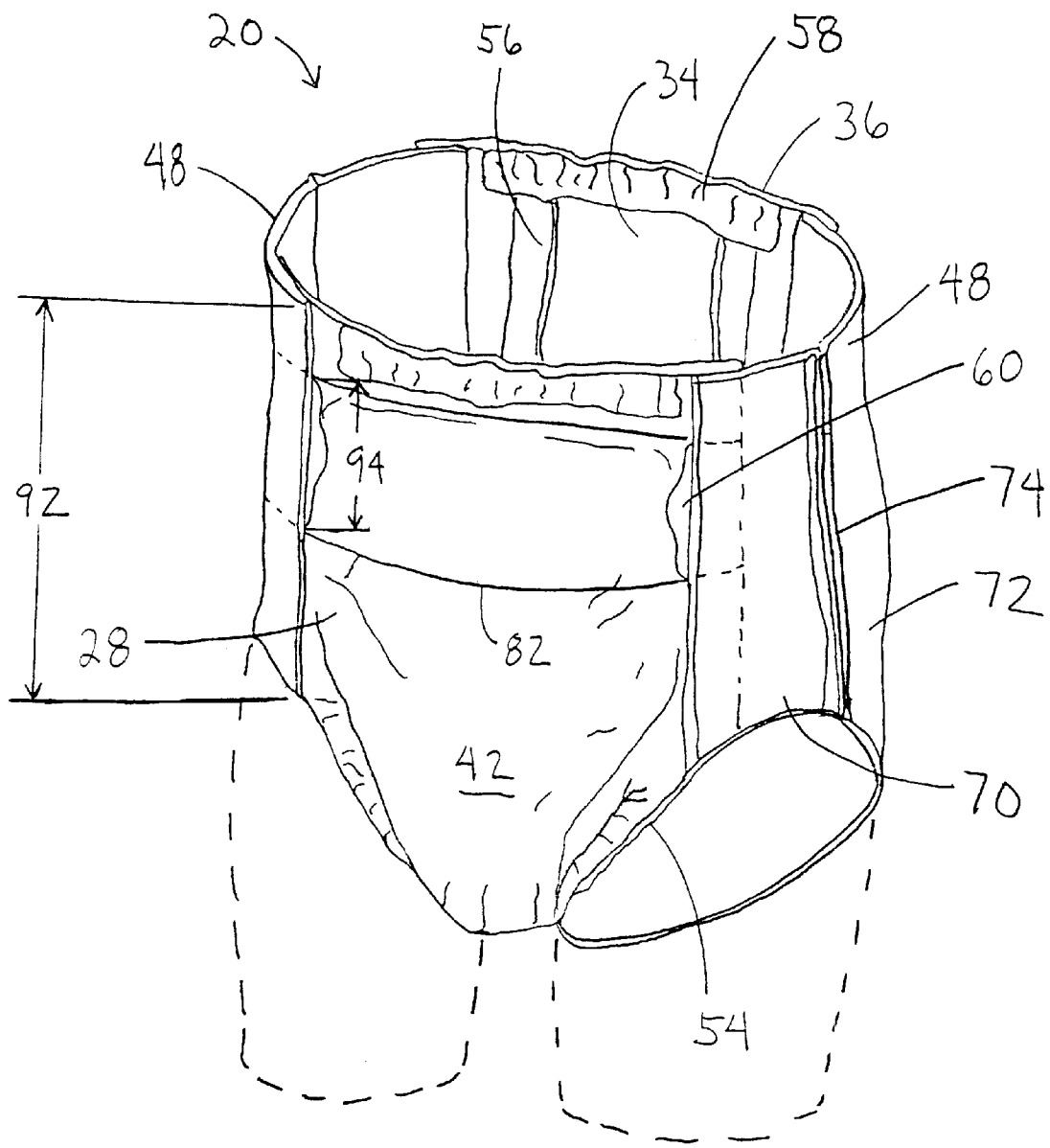
FIG. 1 representatively shows a perspective view of an example of a pant-like, disposable absorbent article of the present invention.
Figure 2:
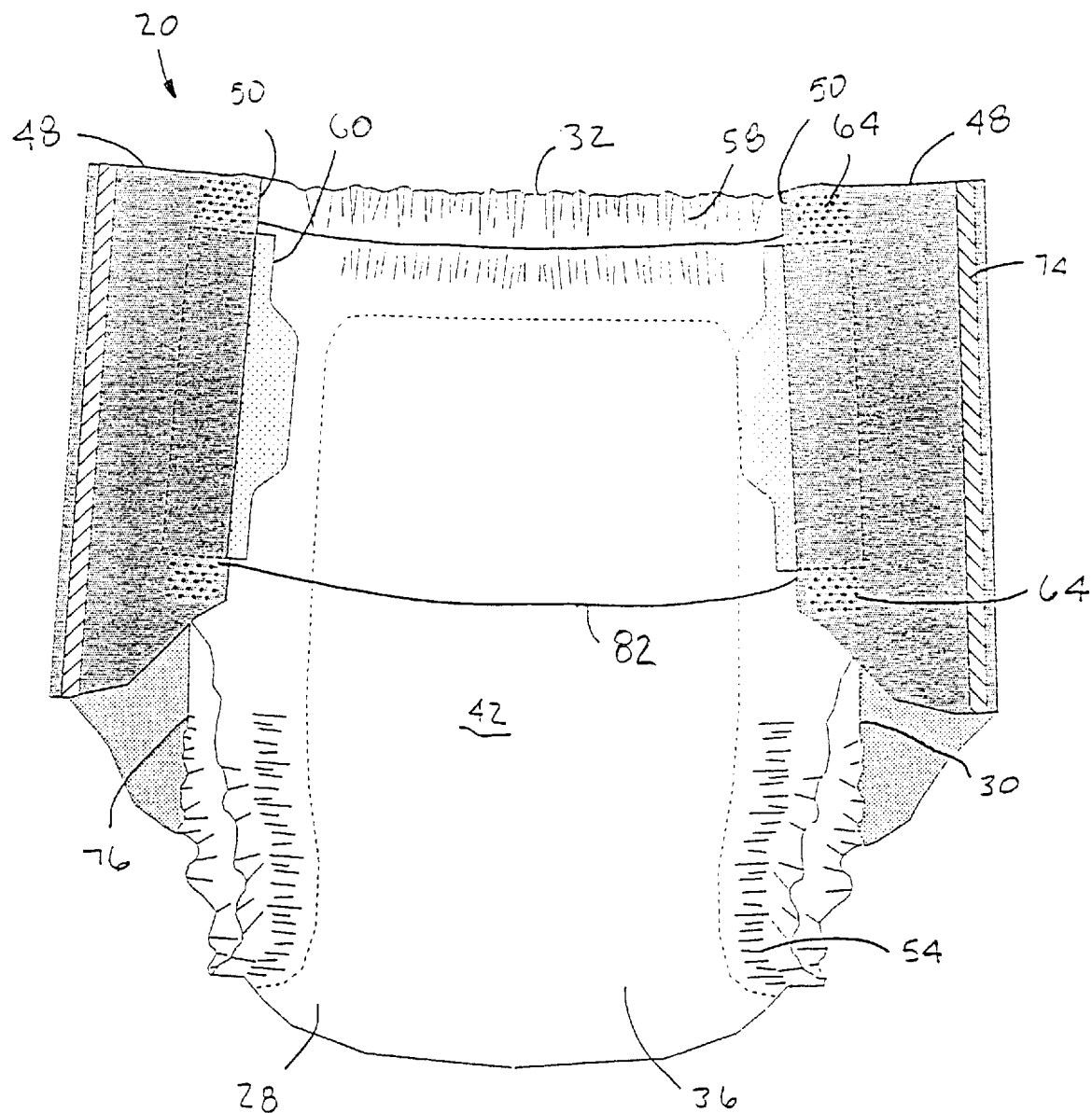
FIG. 2 representatively shows a front plan view of the pant-like, disposable absorbent article of FIG. 1.
Figure 3:
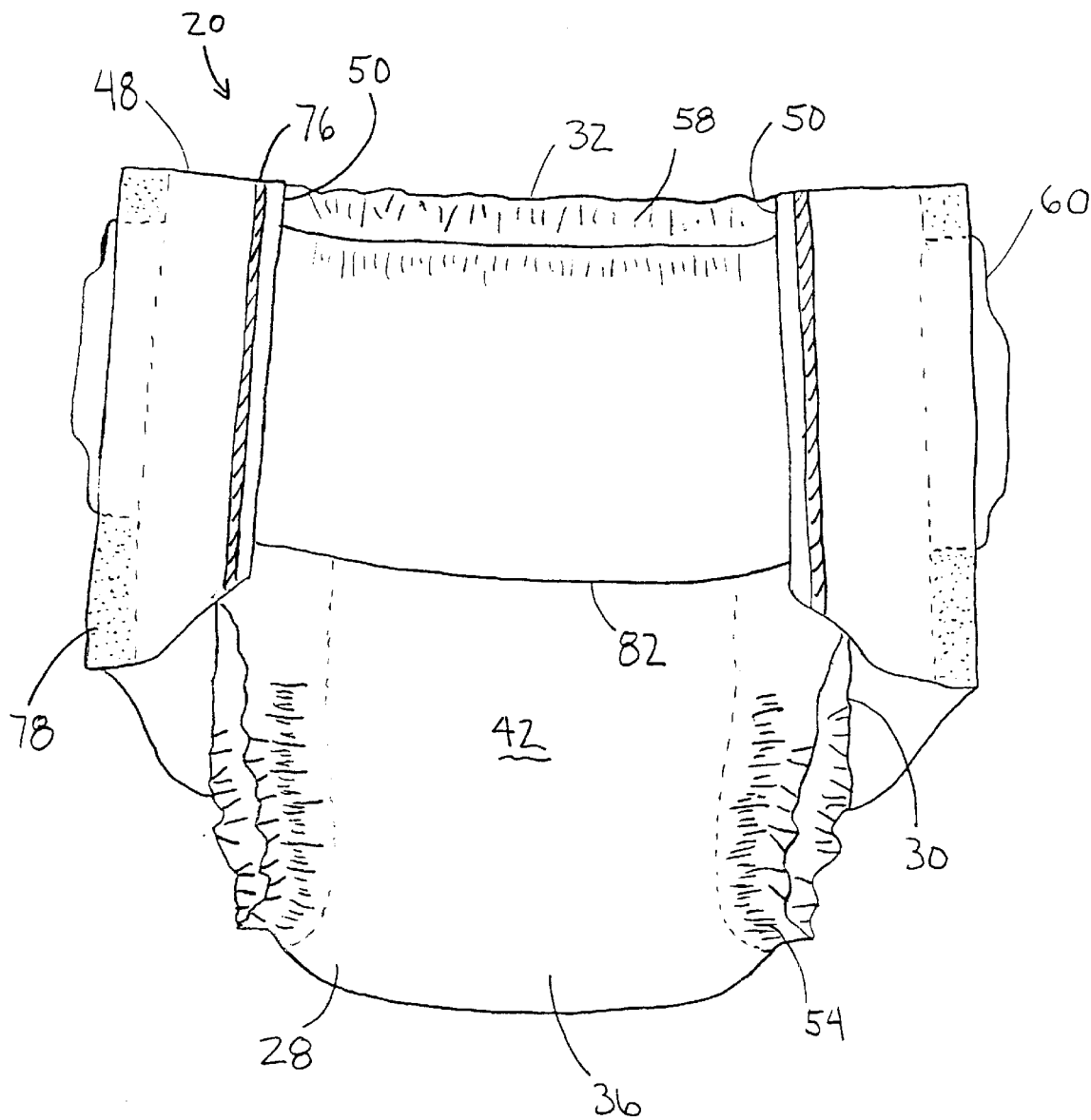
FIG. 3 representatively shows a front plan view of an alternate configuration of the folded fasteners of the absorbent article of FIG. 1, wherein the folded fasteners are located within the releasable joints located at the side seams.

FIG. 1 representatively illustrates an example of a pant-like, disposable diaper, as generally indicated at 20, of the present invention. FIG. 2 representatively illustrates a front plan view of the pant-like diaper of FIG. 1. FIG. 3 representatively illustrates a front plan view of an alternative configuration of the folded fasteners of the pant-like diaper 20.

Figure 4:
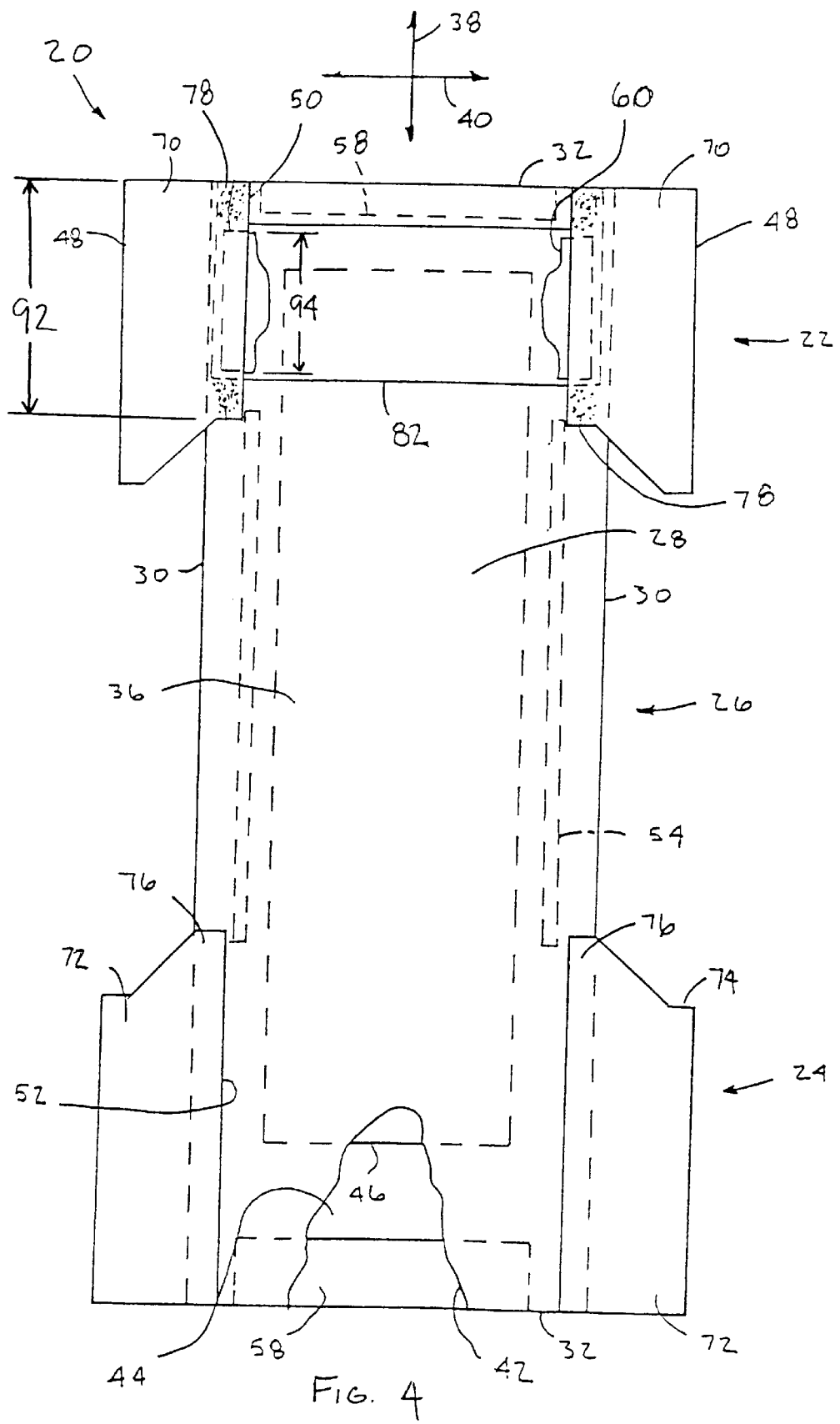
FIG. 4 representatively shows a plan view of the disposable absorbent article of FIG. 1 with the permanent joints broken and in a stretched and laid flat condition with the surface of the article which contacts the wearer's clothing facing the viewer and with portions of the article partially cut away to show the underlying features.

FIG. 4 representatively illustrates the pant-like diaper of FIG. 1 with the permanent joints broken and in a stretched and laid flat configuration with the surface of the diaper adapted to contact the wearer's clothing facing the viewer and with portions of the diaper partially cut away to show the underlying features. As illustrated in FIG. 4, the diaper 20 defines a front waist region 22, a back waist region 24, a crotch region 26 which extends between and connects the front and back waist regions 22 and 24, a longitudinal direction 38 and a lateral direction 40.

The illustrated pant-like diaper 20 includes an absorbent chassis 28 and a pair of laterally opposed side panels 48. The absorbent chassis 28 defines a pair of laterally opposed side edges 30, a pair of longitudinally opposed waist edges 32, an interior surface 34 which is configured to contact the wearer, and an exterior surface 36 opposite the interior surface 34 which is configured to contact the wearer's clothing in use. The absorbent chassis 28, as representatively illustrated in FIG. 4, includes an outer cover 42, a bodyside liner 44 which is connected to the outer cover 42 in a superposed relation, and an absorbent core 46 which is located between the outer cover 42 and the bodyside liner 44. The side panels 48 extend laterally outward from and between each opposed side edge 30 of the absorbent chassis 28 in the front and back waist regions 22 and 24.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The side panels 48 comprise the portions of the diaper which, when worn, are positioned on the side hip regions of the wearer. The laterally opposed side edges 30 of the absorbent chassis 28 and the side panels 48 of the diaper 20 generally define leg openings which may be curvilinear. The waist edges 32 of the absorbent chassis 28 of the diaper 20 and the side panels 48 are configured to encircle the waist of the wearer when worn and provide a waist opening when attached or fastened which defines a waist perimeter dimension.

As illustrated in FIGS. 1,2, 4, 7 and 9, at least one of the side panels 48 of the pant-like diaper 20 includes a side margin that is releasably attached to the side edge 30 of the absorbent chassis 28 in one of the waist regions 22 or 24 to provide a releasable joint 78. The pant-like diaper 20 further includes at least one folded fastener 60. The folded fastener 60 is configured to be opened up for use after the releasable joint 78 is disengaged. The folded fastener 60 may be located adjacent or within the releasable joint 78. The illustrated folded fastener may further include an active fastening area 68 which may remain unexposed until the folded fastener 60 is opened for use. The diaper 20 of the present invention may further include an attachment panel 82 located on the exterior surface 36 of the absorbent chassis 28 to which the folded fastener 60 is configured to releasably engage.

The absorbent chassis 28 is configured to contain and/or absorb any body exudates discharged from the wearer. Whereas, the side panels 48, releasable joints 78, and the folded fasteners 60 are configured to maintain the diaper 20 about the waist of the wearer and provide a pant-like appearance. The diaper 20 may further include leg elastics 54, containment flaps 56 and waist elastics 58 as are known to those skilled in the art. It should be recognized that individual components of the diaper 20 may be optional depending upon the intended use of the diaper 20.

The pant-like diaper 20 may be of various suitable shapes. For example, in the opened configuration as illustrated in FIG. 4, the diaper may have an overall rectangular shape, T-shape or an approximately hour-glass shape. In the shown embodiment, the diaper 20 has a generally I-shape in an open configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 46 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 46 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the absorbent chassis 28 of the pant-like diaper 20, as representatively illustrated in FIGS. 1–5, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 46. Still further, the outer cover 42 may optionally be composed of a micro-porous "breathable" material which permits vapors to escape from the absorbent 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

The bodyside liner 44, as representatively illustrated in FIG. 4, suitably presents a bodyfacing surface which is compliant, soft feeling, and nonirritating to the wearer's skin. Further, the bodyside liner 44 may be less hydrophilic than the absorbent core 46, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 46.

Various woven and nonwoven fabrics can be used for the bodyside liner 44. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto which is configured to treat or be transferred to the wearer's skin. The absorbent core 46 of the pant-like diaper 20, as representatively illustrated in FIGS. 4, and 6–9, may suitably comprise a matrix of hydrophilic fibers, such as a web of cellulosic fluff, mixed with particles of a high-absorbency material commonly known as superabsorbent material. In a particular embodiment, the absorbent core 46 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 46 to better contain and absorb body exudates. The concentration of the superabsorbent particles may also vary through the thickness of the absorbent core 46. Alternatively, the absorbent core 46 may comprise a laminate of fibrous webs and superabsorbent material or other suitable means of maintaining a superabsorbent material in a localized area.

The absorbent core 46 may have any of a number of shapes. For example, the absorbent core may be rectangular, I-shaped, or T-shaped. It is generally preferred that the absorbent core 46 be narrow in the crotch area of the diaper 20. It has been found that the absorbent core 46 of the present invention is particularly useful when the width dimension in the crotch region 26 is from about 2.5 to about 12.7 centimeters (1.0 to about 5.0 inches), and desirably no more than about 7.6 centimeters (3.0 inches). The narrow crotch width dimension of the absorbent core 46 allows the absorbent chassis 28 to better fit between the legs of the wearer. The size and the absorbent capacity of the absorbent core 46 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrilegrafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent core 46.

Optionally, a substantially hydrophilic tissue wrapsheet (not illustrated) may be employed to help maintain the integrity of the airlaid fibrous structure of the absorbent core 46. The tissue wrapsheet is typically placed about the absorbent core over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent core. The wrapsheet material on one side of the absorbent fibrous mass may be bonded to the wrapsheet located on the opposite side of the fibrous mass to effectively entrap the absorbent core 46.

Figure 5:
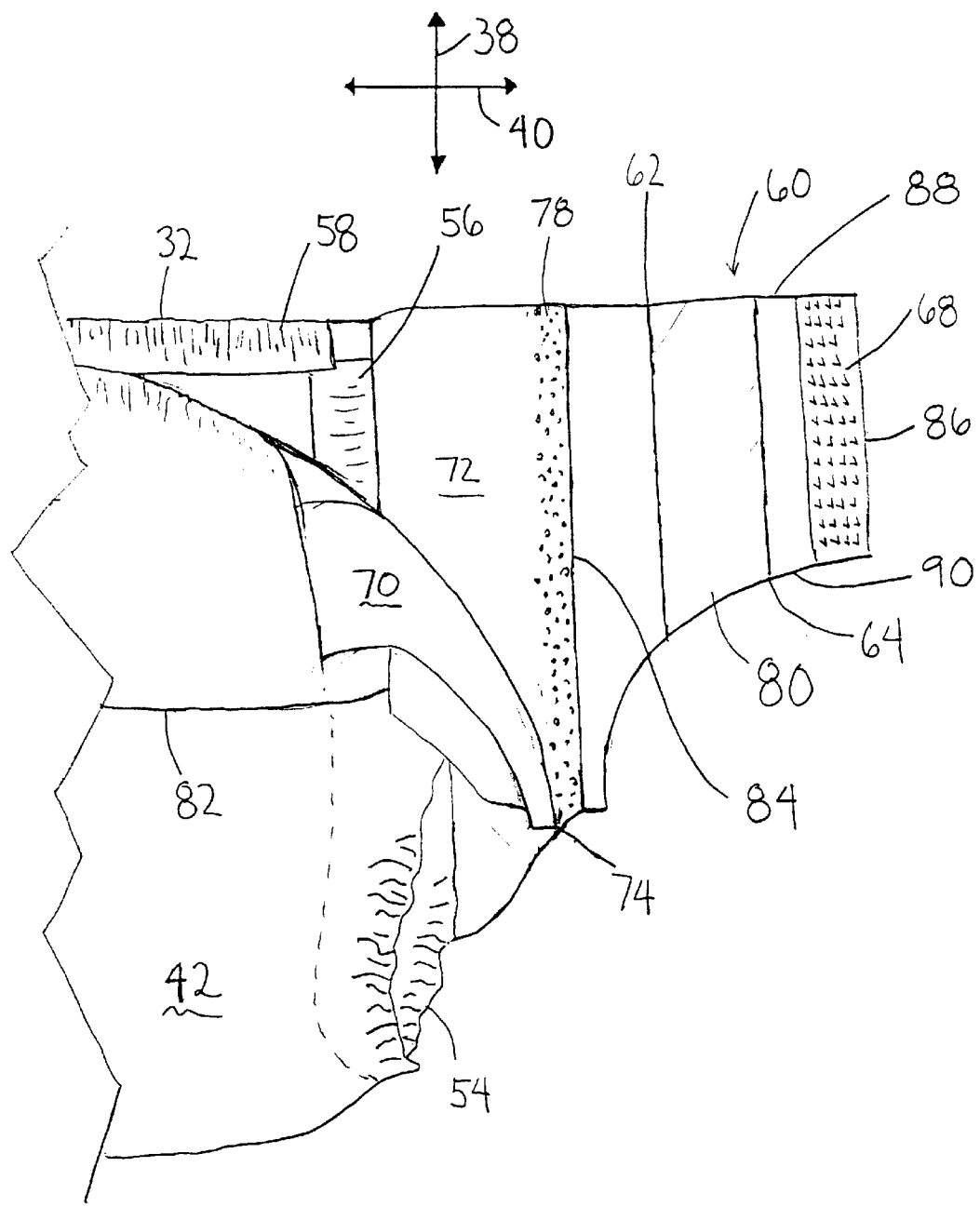
FIG. 5 representatively shows a portion of the front plan view of the pant-like, disposable absorbent article of FIG. 3, wherein the releasable joint is disengaged and the folded fastener is fully opened for use.

As representatively illustrated in FIGS. 1 and 5, the absorbent chassis 28 of the pant-like diaper 20 may include a pair of containment flaps 56 which are configured to provide a barrier to the lateral flow of body exudates. The containment flaps 56 may be located along the laterally opposed side edges 30 of the absorbent chassis 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent chassis 28 or may only extend partially along the length of the absorbent chassis 28. When the containment flaps 56 are shorter in length than the absorbent chassis 28, the containment flaps 56 can be selectively positioned anywhere along the side edges 30 of the absorbent chassis 28. In a particular aspect of the invention, the containment flaps 56 extend along the entire length of the absorbent chassis 28 to better contain the body exudates.

Such containment flaps 56 are generally well known to those skilled in the art. For example, suitable constructions and arrangements for containment flaps 56 are described in U.S. Pat. No. 4,704,116 issued Nov. 3, 1987, to K. Enloe the disclosure of which is hereby incorporated by reference.

The disposable pant-like diaper 20 of the different aspects of the present invention may further include elastics at the waist edges 32 and side edges 30 of the absorbent chassis 28 to further prevent leakage of body exudates and support the absorbent chassis 28. For example, as representatively illustrated in FIGS. 1–5, the pant-like diaper 20 of the present invention may include a pair of leg elastic members 54 which are connected to the laterally opposed side edges 30 of the absorbent chassis 28 in the crotch region 26 of the diaper 20 and a pair of waist elastic members 58 which are connected to the longitudinally opposed waist edges 32 of the absorbent chassis 28 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

As representatively illustrated in FIGS. 1–9, the pant-like diaper 20 further includes a pair of laterally opposed side panels 48. Each side panel 48 defines a first side margin 50 which is joined to the side edge 30 of the absorbent chassis 28 in the front waist region 22 and a second side margin 52 which is joined to the side edge 30 of the absorbent chassis 28 in the back waist region 24. At least one of the side margins 50 or 52 of the side panels 48 may be permanently connected to the side edges 30 of the absorbent chassis 28 in at least one of the waist regions 22 and 24 to provide a permanent joint 76. The opposite side margin 50 or 52 on at least one of the side panels may then be releasably attached to the side edges 30 of the absorbent chassis 28 in the opposite waist region to provide a releasable joint 78. Desirably, both of the side panels 48 include a releasable attachment to provide a pair of releasable joints 78 for improved performance.

For example, as illustrated in FIGS. 1–9, the second side margins 52 of the side panels 48 of the diaper 20 may be permanently secured to and extend laterally beyond the side edges 30 of the diaper 20 in the back waist region 24 of the diaper 20 to provide a permanent joint 76. The side panels 48 may be permanently connected to the diaper 20 along the permanent joint 76 using attachment means known to those skilled in the art such as adhesive, thermal or ultrasonic bonding. As discussed above, the side panels 48 are desirably permanently connected to the absorbent chassis 28 of the diaper 20 using ultrasonic bonding for improved manufacturing efficiency and reduced raw material cost. In such a configuration, the first side margin 50 of at least one of and desirably each of the side panels 48 is releasably attached to the side edges 30 of the absorbent chassis 28 in the front waist region 22 of the diaper 20 to provide a releasable joint 78. The releasable joint 78 in such a configuration is located on the front abdominal region of the wearer for easy access to the caregiver.

Alternatively, the side margins of the side panels 48 may be permanently connected to the side edges 30 of the absorbent chassis 28 in the front waist region 22 and releasably attached to the side edges 30 of the absorbent chassis 28 in the back waist region 24 of the diaper if it is desired that the releasable joint 78 be located towards the back of the wearer. Such a configuration may be desirable to prevent a wearer from unfastening the article prematurely. Still further, as discussed in more detail below, the side margins of the side panels 48 may be permanently connected to the side edges 30 of the absorbent chassis 28 in both the front and back waist regions 22 and 24. For such a configuration, the side panels 48 may include at least 2 individual panels that are releasably connected together to provide the releasable joints 78.

The releasable joints 78 may be provided by the folded fasteners 60 and/or any type of bonding, such as adhesive, thermal and ultrasonic bonding as are well known to those skilled in the art. The bonds may be discrete point bonds, dashed lines, continuous lines, discontinuous lines and the like, or combinations thereof. Moreover, the bonds may have any shape such as circular, square, triangular and the like. Desirably, the bonds are ultrasonic point bonds for improved manufacturing efficiency. In such a configuration, the ultrasonic bonds will be destroyed upon the first disengagement of the releasable joints 78.

The diaper 20 is provided in a pant-like configuration with the releasable joints 78 intact. In such a configuration, the diaper 20 may be pulled on or off over the legs and hips of the wearer. Further, the releasable joints 78 should have a relatively low peel strength such that the joint can be broken by the caregiver if desired without tearing or severely damaging the other portions of the diaper 20. As such, the releasable joints 78 may be disengaged to inspect the diaper for possible soiling. If the diaper 20 is soiled during use, the releasable joints 78 may be disengaged to easily remove the diaper 20 from the waist of the wearer with reduced risk of undesirably soiling the clothes or legs of the wearer. Finally, the releasable joints 78 may also be disengaged to allow the user the option of applying the pant-like diaper 20 in a conventional diaper configuration.

Each of the side panels 48 may include one or more individual, distinct pieces of material. For example, in the illustrated embodiments, each side panel 48 includes a front side panel 70 and a back side panel 72. The illustrated front side panel 70 includes the first side margin 50 which is releasably attached to the side edges 30 of the absorbent chassis 28 in the front waist region 22 of the diaper 20 to provide the releasable joint 78. The illustrated back side panel 72 includes the second side margin 52 which is permanently connected to the side edges 30 of the absorbent chassis 28 in the back waist region 24 of the diaper 20 to provide the permanent joint 76. In such a configuration, the laterally outward edge of each front side panel 70 is connected to the laterally outward edge of each back side panel 72 to provide a side seam 74 as illustrated in FIGS. 1–2, 5, 7 and 9. Desirably, the laterally outward edges of the front and back side panels 70 and 72 are attached to each other along the side seam 74 using ultrasonic bonding for improved manufacturing efficiency and reduced raw material cost. Side panels 48 having such front and back side panels 70 and 72 provide improved manufacturability. In an alternative configuration, each side panel 48 may include a single piece of material which is folded over upon itself during manufacturing along a fold line located in a similar location to the side seam 74.

Figure 6:
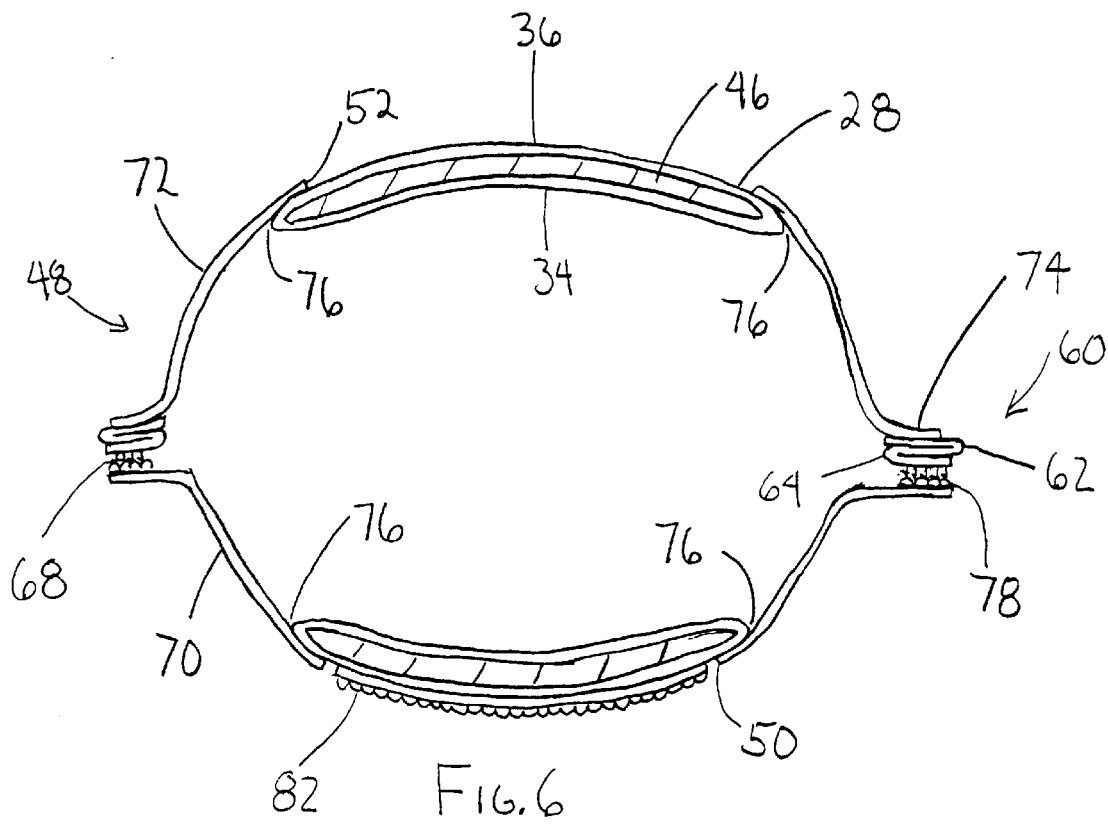
FIG. 6 representatively shows a lateral cross section of the pant-like, disposable absorbent article of FIG. 3.
Figure 8:
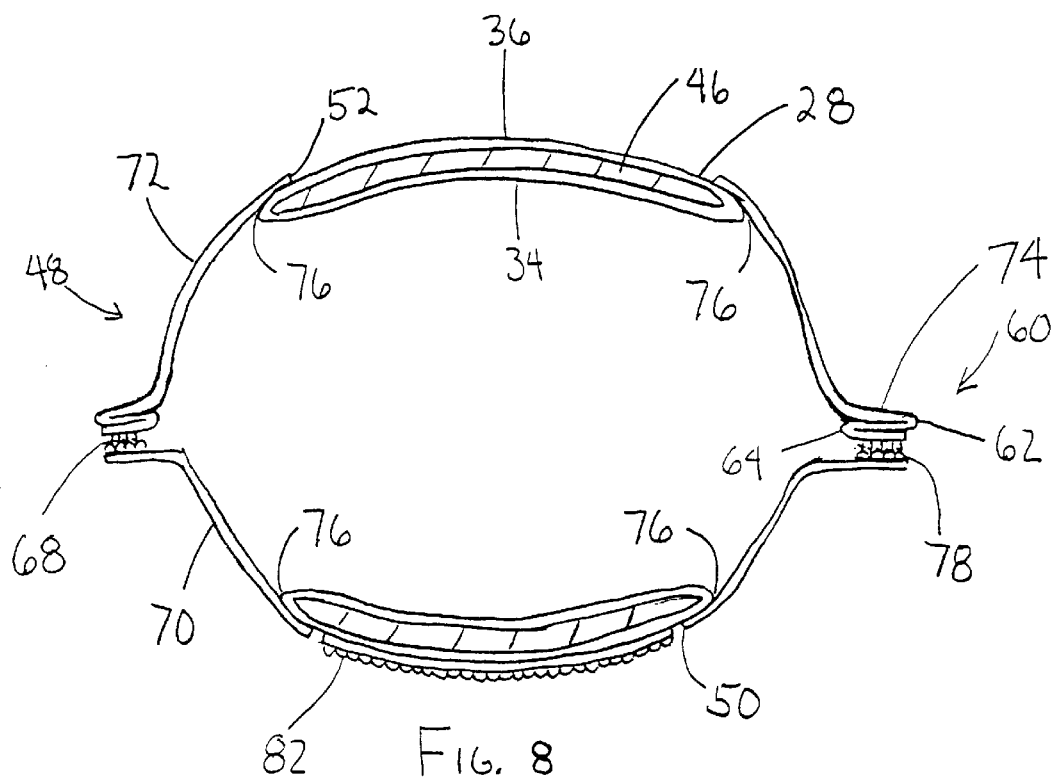
FIG. 8 representatively shows a lateral cross section of an alternate configuration of the folded fasteners of FIG. 3, wherein the folded fasteners are provided by a portion of the side panels.

In one embodiment, as illustrated in FIGS. 3, 6 and 8, the side seams 74 may alternatively provide the releasable joint 78. In such a configuration, the first side margin 50 of the front side panels 70 are permanently attached to the side edges 30 of the absorbent chassis 28 in the front waist region 22. Likewise, the second side margin 52 of the back side panels 72 are permanently attached to the side edges 30 of the absorbent chassis 28 in the back waist region 24. The releasable joint 78 is created by the releasable attachment of the laterally outward edges of the front side panel 70 and the back side panel 72 at the side seam 74.

The side seams 74 of the present invention may be arranged in a number of configurations. For example, as representatively illustrated in FIGS. 6–9, the side seams 74 may be provided in a flange bonded configuration. In the illustrated embodiments the interior surface of the front panel 70 is attached to the interior surface of the back panel 72 in an overlapping configuration to provide the flanged side seams 70. Alternatively, the side seams 74 may be provided in a lap bonded configuration. As such, the exterior surface 36 of one of the front or back panels 70 and 72 are bonded to the interior surface 34 of the opposing front or back panel 70 and 72 in an overlapping arrangement. For example, the side seams 74 may be provided in a lap bonded configuration similar to that illustrated by the permanent joints 76 in FIGS. 6 and 8. Such a configuration may be desirable when the side seams 74 provide the releasable joints 78, as a lap bonded configuration would subject the side seams 74 primarily to shear forces during use, thereby providing enhanced seam strength.

In a particular embodiment, the releasable joints 78 may be provided by a combination of permanent bonds and perforations. For example, the first and second side margin 50 and 52 of the side panels 48 may be permanently attached to the side edges 30 of the absorbent chassis 28 in the front and back waist region 22 and 24, respectively. At least one of the permanent joints 76 may be made releasable by a line of perforations made in the longitudinal direction 38 from the waist opening to the leg opening adjacent the permanent joint 76. Similarly, should the side panels 48 be provided by front and back side panels 70 and 72, the line of perforations may be provided adjacent the side seams 74 such that the releasable joint 78 is at the side seams 74.

Materials suitable for the side panels 48 of the diaper 20 are generally known to those skilled in the art. For example, suitable materials for the side panels 48 include those materials described above as being suitable for the outer cover 42 or bodyside liner 44 of the absorbent chassis 28 of the diaper 20 such as woven and nonwoven materials or laminates of such materials. Desirably, the side panels 48 are elastic or stretchable to provide improved fit about the wearer. For example, the side panels 48 may comprise a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13,1993 to Mormon, and European Patent Application No. EP 0 217 032 published on Apr. 8,1987 in the names of Taylor et al., the disclosures of which are hereby incorporated by reference. When made with elastic materials, the side panels 48 are desirably capable of elongating in the lateral direction 40 from about 10 to about 400 percent, more desirably at least about 100 percent, even more desirably from about 100 to about 300 percent, and still yet more desirably from about 150 to about 250 percent for improved fit and performance. The stretchability of the side panels 48 allows the side panels 48 to stretch over and around the hips of the wearer as the pant-like diaper is pulled on while still maintaining proper fit at the waist after the diaper is correctly positioned on the wearer.

Desirably, the side panels 48 are a neck-bonded laminate material for improved manufacturing due to its ability to stretch in the cross machine direction. For example, in a particular embodiment, the side panels 48 include a neck-bonded laminate material which includes a urethane film having a basis weight of about 15 grams per square meter and commercially available from Shawmut Mills, a business having offices in West Bridgewater Mass., under the trade designation SHAWMUT TX-1560 sandwiched between two layers of necked, stretched spunbond. Each spunbond layer has a basis weight of about 16 grams per square meter and is composed of 3.0 denier polypropylene fibers. The composite is laminated together with an adhesive spray at an add-on rate of about 0.3 grams per square meter. A suitable adhesive is available from Findley Adhesive under the trade designation FINDLEY 2525A. Such a neck-bonded laminate material is generally capable of elongating in the cross machine direction about 185 percent.

The pant-like disposable diaper 20 of the different aspects of the present invention further includes at least one folded fastener 60 for securing the absorbent article about the waist of the wearer when the at least one releasable joint 78 is disengaged. Desirably, the diaper 20 includes a pair of folded fasteners 60 and a pair of releasable joints 78 as illustrated in FIGS. 1–9 for improved fit and performance. Upon the disengagement of the releasable joints 78, the folded fasteners 60 may be opened, exposing the active fastening areas 68 of the folded fasteners 60. The active fastening areas 68 are configured to releasably engage other portions of the diaper 20 to maintain the diaper on the wearer after the releasable joints 78 have been disengaged. Therefore, the diaper 20 of the present invention provides the ease of application of a pant-like absorbent article while yet being capable of providing the fit and comfort and ease of application of a typical diaper type absorbent article.

The folded fasteners 60 may be comprised of a single piece of material or a plurality of pieces. Moreover, a portion of the diaper 20 such as the side panels 48 may provide the folded fastener 60. The folded fastener 60 may be fashioned in various shapes and sizes as are known to those skilled in the art. For example, as representatively illustrated in FIGS. 10 and 11, the folded fastener 60 may be generally rectangular in shape. Alternatively, the folded fastener 60 may have other shapes well known to those skilled in the art.

Desirably, the folded fasteners 60 may define a length in the longitudinal direction that is smaller than the length of the releasable joint 78 in the longitudinal direction. For example, as representatively illustrated in FIGS. 1 and 4, the releasable joint 78 may define a length 92 in the longitudinal direction 38 that is greater than a length 94 of the folded fastener 60. In such a configuration, the length 92 of the releasable joint 78 is sufficient to effectively provide the diaper 20 in a pant-like configuration. Whereas, when the releasable joint 78 is broken, the length 94 of the fastener 60 is not too great, such that the diaper may be effectively used in a conventional diapering configuration also. As such, the folded fastener 60, sized to be relatively smaller in the longitudinal direction 38 than the releasable joint 78, desirably reduces redmarking and discomfort of the wearer which may occur if the fastener 60 is provided as large or nearly as large as the releasable joint 78 in the longitudinal direction 38. However, the folded fastener 60 still advantageously provides a fastener which is sized to provide effective diaper fastening.

Moreover, the relatively shorter length 94 of the folded fastener 60 allows the hips and legs of the wearer a fuller range of motion thereby further enhancing the fit and comfort of the diaper on the wearer.

In a particular embodiment, the length 94 of the folded fastener 60 in the longitudinal direction 38 may be from 10 percent to about 80 percent and desirably from about 20 percent to about 50 percent of the total length 92 of the releasable joint 78. For example, if the length 92 of the releasable joint 78 was approximately 5 inches, then the length 94 of the folded fastener 60 may desirably be from about 1 inch to about 2.5 inches. Desirably, to provide effective fastening, the length 94 of the folded fastener 60 may be from about 0.75 inches to about 3 inches.

In a particular embodiment, the length 92 of the releasable joint 78 to the length 94 of the folded fastener 60 may be accomplished as representatively illustrated in FIG. 5. For example, the folded fasteners 60 may have a curvilinear shape which is tapered from the inboard edge 84 of the folded fastener 60 to the outboard edge 86 of the folded fastener 60 to desirably accommodate the legs of the wearer. The length of the inboard edge 84 of the folded fastener 60 in the longitudinal direction 38 may generally correspond to the length 92 of the releasable joint 78. Similarly, the length of the outboard edge 86 of the folded fastener 60 in the longitudinal direction 38 may generally correspond to the desirable relative length 94 of the folded fastener 60. As such, the tapered folded fasteners 60 desirably provide the hips and legs of the wearer with a full range of motion, thereby enhancing the fit and comfort of the wearer, as described above. Moreover, since such a configuration may allow for the inboard edge 84 of the folded fastener 60 to be generally equal in length in the longitudinal direction 38 to the length 92 of the releasable joint 78, the folded fastener 60 may, upon use, effectively provide the secure fit and comfort of a conventional training pant. Alternatively, the folded fasteners 60 may be tapered from the inboard edge 84 to the outboard edge 86 in other suitable manners such as a linear taper, a stepped taper, or the like.

The folded fasteners 60 may be configured to have the active fastening area 68 exposed when in the folded position. Alternatively, the folded fasteners 60 may be configured such that the active fastening areas 68 remain unexposed to the wearer or the wearer's clothing when the folded fasteners 60 are folded in preparation for use. As such, the opportunity for irritation of the wearer's skin is lowered, and the application of the diaper 20 is eased as inadvertent snagging of the folded fasteners 60 with the wearer's clothing and the diaper 20 is diminished.

The folded fastener may be folded in any configuration known to those skilled in the art.

Figure 7:
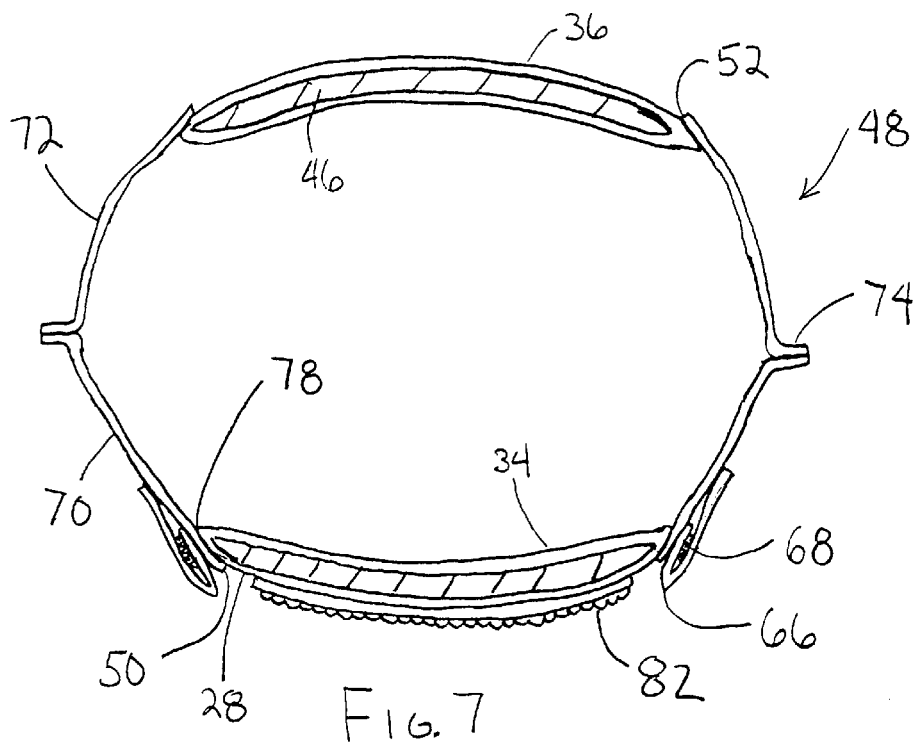
FIG. 7 representatively shows a lateral cross section of an alternate configuration of the folded fasteners of FIG. 1, wherein the folded fasteners are located on the exterior surface of the article adjacent the releasable joint.
Figure 9:
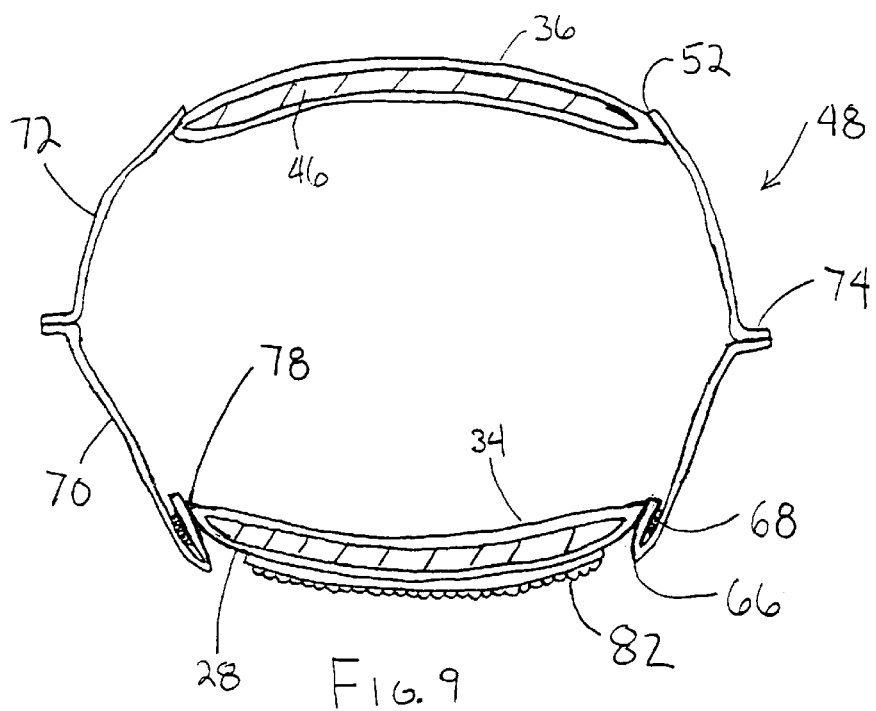
FIG. 9 representatively shows a lateral cross section of an alternate configuration of the folded fasteners of FIG. 1, wherein the folded fasteners are located on the exterior surface of the article adjacent the releasable joint and are provided by a portion of the side panels.

For example, as representatively illustrated in FIGS. 7, 9, and 11, the folded fasteners 60 of the present invention may be provided as a j-fold fastener. For example, the folded fastener may include a single fold 66, and an active fastening area 68 desirably located laterally outboard from the single fold 66. The folded fastener may be folded upon itself at the single fold 66 to provide the j-fold configuration. The j-fold fastener may be folded upon itself in either direction thereby either exposing the active fastening area 68 or providing the folded fastener 60 with the active fastening area 68 unexposed. The j-fold configuration has the advantage of providing a fastener which advantageously eases the manufacturing process thereby lowering manufacturing and material costs. Moreover, when in the folded position, the j-fold configuration provides a fastener which may be thinner than other folded configurations, thereby enhancing the fit and comfort of the wearer, particularly when the fastener 60 is provided in an area of the diaper 20 that requires flexibility with movement of the wearer.

Alternatively, as representatively illustrated in FIGS. 5–6, 8, and 10, the folded fasteners 60 of the present invention may be provided as a z-fold fastener. For example, the folded fastener may include a first fold 62, a second fold 64 located laterally outboard from the first fold 62, and an active fastening area 68 desirably located laterally outboard from the second fold 64. The folded fastener may be folded upon itself at the first and second folds 62 and 64 to provide the z-fold configuration. The folded fastener may also include a front side 63 and a back side 65, with the active fastening area 68 located on the front side 63. The front side 63 of the folded fastener may be folded upon itself at the first fold 62, and the back side 65 of the folded fastener may be folded upon itself at the second fold 64 to provide the z-folded fastener with the active fastening area 68 exposed. Alternatively, the back side 65 of the folded fastener may be folded upon itself at the first fold 62, and the front side 63 of the fastener may be folded upon itself at the second fold 64, providing the z-fold fastener with the active fastening area 68 unexposed. This particular configuration has the advantage of supplying a fastener which is large in the lateral direction 40, but provided within a small surface area of the diaper. As such, the z-folded fastener, in use, allows the active fastening area 68 greater range to engage the diaper 20 in a variety of locations, thereby enhancing the fit of the diaper 20 on the wearer.

The folded fastener of the present invention may further include an extensible panel 80. For example, as representatively illustrated in FIG. 5, the folded fasteners 60, when provided in a z-folded configuration, may include an extensible panel 80 between the first and second fold 62 and 64. Alternately, the folded fasteners 60 may include an extensible panel in any location or any fold configuration. Thus, the extensible panel 80 would provide improved fit and comfort to the wearer by allowing the folded fastener 60 more flexibility and range in engaging the exterior surface 36 of the diaper 20. The extensible panel 80 may be comprised of material well known in the art. The materials may include a stretch-bonded-laminate (SBL) material, a neck-bonded-laminate (NBL) material, an elastomeric film, an elastomeric foam material, or the like such as described above as being suitable for the side panels 48.

The folded fasteners 60 are provided in combination with the releasable joints 78. As such, upon disengagement of the releasable joints 78, the folded fasteners 60 in the illustrated embodiments are configured to be unfolded and used in conjunction with the side panels 48 to refastenably engage the back waist region 24 of the diaper 20 to the front waist region 22 of the diaper 20. When the side panels 48 are extensible, this arrangement advantageously provides the caregiver or the wearer with the added stretch from the side panels 48 while refastenably attaching the fasteners 60 to the front waist region 22 of the diaper 20. Therefore, the wearer is provided with a closer and more conforming fit, thereby reducing the possibility of leakage.

Alternatively, the releasable joint 78 and the folded fastener 60 may be located in the back waist region 24 of the diaper 20. In such a configuration, the folded fasteners 60 would engage the side panels 48 to the back waist region 24 to provide the diaper 20. This configuration may be advantageous when it is desired that the releasable joint 78 and the folded fasteners 60 be located towards the back of the wearer. Such a configuration may be desirable to prevent a wearer from unfastening the article or the folded fasteners 60 prematurely.

In yet another alternative, wherein the releasable joint 78 is provided by the side seam 74, the folded fasteners 60 may be configured to refastenably engage the front side panel 70 to the back waist region 24 or the back side panel 72 to the front waist region 22 to provide the diaper 20. Upon the disengagement of the releasable joints 78 and use of the folded fasteners 60, the wearer is provided with added comfort and flexibility at the joint of the leg and the torso as the fasteners 60 may not be as long in the longitudinal direction as the side seams 74 of the diaper 20.

The folded fasteners 60 may be provided in combination with the releasable joint 78 in any configuration known to those skilled in the art. For example, as representatively illustrated in FIGS. 7 and 9, the folded fasteners 60 may be permanently attached to the diaper 20 adjacent the releasable joint 78 on the exterior surface 36 of the diaper 20. This arrangement provides the advantage of ease of manufacturability and ready accessibility of the folded fastener to the caregiver or wearer for use. Alternatively the folded fasteners 60 may be permanently attached to the diaper 20 adjacent the releasable joint 78 on the interior surface 34 of the diaper 20. Such a configuration may be desirable to prevent a wearer from easily accessing the folded fasteners 60 and providing a neat diaper appearance. Further, the permanent attachment of the folded fasteners 60 to the diaper may be arranged such that the folded fasteners 60 are subjected primarily to peel forces or primarily to shear forces when the fastener is in use.

Alternatively, as representatively illustrated in FIGS. 1–4, 6, and 8 the folded fasteners 60 may advantageously be configured to be located within the releasable joints 78. This configuration provides the advantage of keeping the folded fasteners 60 unobtrusive while the diaper 20 is used in the pant-like arrangement, but makes the folded fasteners 60 readily available and obvious upon disengagement of the releasable joint 78. Moreover, the active fastening area 68 of the folded fastener may be used to assist in maintaining the releasable joint 78 engaged until disengaged by the wearer or caregiver. For example, as representatively illustrated in FIG. 6, the folded fastener may be arranged to have the active fastening area 68 exposed as described above, making it available for use within the releasable joint 78. This arrangement provides the advantage of reducing the need for redundant materials and may reduce the bonding materials and/or process required to provide the releasable joints 78.

In yet another alternative, the folded fasteners 60 of the present invention may be provided by a portion of the diaper 20. For example, as representatively illustrated in FIGS. 8–9, a portion of the side panels 48 may include an active fastening area 68. This portion of the side panels 48 may be folded upon themselves and releasably connected to the absorbent chassis 28 providing the folded fastener and the releasable joint 78. As such, when the wearer or the caregiver disengages the releasable joint 78, the folded portions of the side panels 48 are accessible and provide the folded fasteners 60 for use. The folded fasteners 60 may then be opened and used in combination with the side panels 48 to refastenably connect the front waist region 22 of the diaper 20 to the back waist region 24 of the diaper 20. Alternatively, the side panels 48 may be configured to extend beyond the releasable joint 78, providing excess material which may accordingly be arranged to provide the folded fastener on the exterior surface 36 of the diaper 20. As such, the releasable joint 78 may be disengaged by the wearer or caregiver, at which point the excess material of the side panels 48 may be unfolded and used in combination with the side panels 48 to refastenably connect the back waist region 24 of the diaper 20 to the front waist region 22 of the diaper 20. In each of the above examples, the folded portion of the side panels 48 may be arranged to provide the folded fasteners 60 in any folded configuration, such as a j-folded or a z-folded configuration. By providing the folded fasteners 60 with a portion of the diaper 20, manufacturing and material costs are advantageously reduced as the number of added components to be made and attached to the diaper 20 are reduced.

Desirably, the folded fasteners 60 may be configured to refastenably engage directly with the exterior surface of the outer cover 42 of the diaper 20 to provide improved fit and ease of fastening. Alternatively, an attachment panel 82 may be located on the outer cover 42 to which the folded fasteners are configured to refastenably engage. As representatively illustrated in FIGS. 1–9, the disposable diaper 20 of the present invention may include an attachment panel 82 located on the outer cover 42 in one of the waist regions 22 and 24 on the exterior surface 36 of the diaper 20. In such a configuration, the folded fasteners 60, are configured to refastenably engage the attachment panel 82 to maintain the diaper 20 about the waist of the wearer after the releasable joints are broken and the folded fasteners are unfolded for use. The attachment panel 82 may include two separate panels located along the opposed side edges 30 of the diaper 20 in one of the waist regions 22 and 24 of the diaper 20. Alternatively, the attachment panel 82 may include a single piece of material that extends substantially across the respective waist region of the diaper 20.

As representatively illustrated in FIGS. 6 and 8, the releasable joint 78 may also include an attachment panel, particularly if the folded fastener 60 is assisting in maintaining the releasable joint intact as described above. An attachment panel may be provided along the entire length of the fastener in the longitudinal direction 38. Alternatively, an attachment panel may be included in only a portion of each releasable joint 78, or a plurality of attachment panels may be included within each releasable joint 78. As such, the active fastening area 68 of the folded fastener 60 would engage the attachment panel within the releasable joint 78 in order to assist in maintaining the releasable joint 78 intact.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIGS. 5–9, the active fastening areas 68 may be hook type fasteners and the outer cover 42 or attachment panel 82 may be configured to function as a complimentary loop type fastener. Desirably, the folded fasteners 60 are hook type fasteners which are refastenably engageable directly with the outer cover 42. Such an arrangement provides the ability to vary the size of the waist opening in very small increments over a wide range to fit the waist of the wearer.

The folded fasteners 60 of the present invention may also include passive bonds (not illustrated) for improved reliability of maintaining the folded fasteners 60 in the folded configuration, until they are intended to be opened for use. The passive bonds may be located on the folded fasteners 60 in any manner which provides the desired integrity of the folded fasteners 60. For example, there may be a line or a plurality of lines of passive bonds in the longitudinal direction 38 to hold the folded fastener in the folded configuration until use. In such a configuration, the wearer or the caregiver would disengage the passive bonds after the release of the releasable joints 78 to open the folded fasteners 60 for refastenable engagement with the outer cover 42 or attachment panel 82 of the diaper 20. The passive bonds may be provided by any type of bonding such as thermal, adhesive, and ultrasonic bonding as are well known to those skilled in the art and may be discrete point bonds, dashed lines, continuous lines, discontinuous lines, and the like or combinations thereof. Moreover, the passive bonds may have any shape such as circular, square, triangular, and the like. Desirably, the passive bonds are ultrasonic point bonds for improved manufacturing efficiency. In such a configuration, the ultrasonic passive bonds will be destroyed upon the opening of the folded fasteners 60.

The different aspects of the present invention advantageously provide pant-like, disposable absorbent articles which can include the combination of releasable joints and folded fasteners 60. The absorbent article is provided in the prefastened, pant-like configuration to allow the absorbent article to be pulled up or down over the hips of the wearer such as conventional training pants. Yet, the releasable joints may be disengaged to allow the diaper to be used and applied as a conventional diaper. Moreover, upon disengagement of the releasable joints, the folded fasteners can be used to refastenably engage and adjust the front and back waist portions of the absorbent article to maintain the absorbent article about the waist of the wearer after the article has been pulled on in a similar manner to conventional diapers.

As a result, the absorbent articles of the present invention are designed to be capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness. As such the present invention provides an absorbent article which performs the dual functions of a pant-like absorbent article and a conventional diaper.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A pant-like, disposable absorbent article which defines a front waist region, a back waist region, a crotch region which extends between and connects said waist regions, a longitudinal direction and a lateral direction, said absorbent article comprising:
   a) an absorbent chassis which defines an absorbent core, an exterior surface, an interior surface opposite said exterior surface, a pair of laterally opposed side edges and a pair of longitudinally opposed waist edges;
   b) a pair of opposed side panels which extend laterally outward from said side edges of said absorbent chassis and connect said front waist region to said back waist region to define a waist opening and a pair of leg openings in said pant-like disposable absorbent article, wherein at least one of said opposed side panels defines a first side margin which is permanently attached to said side edge of said absorbent chassis in one of said waist regions to provide a permanent joint and a second side margin which is releasably attached to said side edge of said absorbent chassis in an opposite waist region of said absorbent article to provide a releasable joint; and
   c) a first folded fastener located adjacent said releasable joint wherein said folded fastener is configured to be unfolded and used to refastenably engage said second side margin of said at least one side panel to said opposite waist region of said absorbent article after said releasable joint is released.

2. The pant-like disposable absorbent article according to claim 1 wherein said folded fastener is a hook and loop type fastener.

3. The pant-like disposable absorbent article according to claim 2 wherein said folded fastener is configured to directly, refastenably engage said exterior surface of said absorbent chassis of said pant-like absorbent article.

4. The pant-like disposable absorbent article according to claim 2 and further comprising at least one attachment panel which is located on said exterior surface of said absorbent chassis of said absorbent article wherein said folded fastener is directly refastenably engageable to said attachment panel.

5. The pant-like disposable absorbent article according to claim 1 wherein said second side margin of said at least one side panel is releasably attached to said side edge of said absorbent chassis in said front waist region of said absorbent article to provide said releasable joint and wherein said first side margin of said at least one side panel is permanently attached to said side edge of said absorbent chassis in said back waist region to provide said permanent joint.

6. The pant-like disposable absorbent article according to claim 1 wherein each of said side panels includes a front panel refastenably attached to said side edges in said front waist region of said absorbent article to provide said releasable joints and a back panel attached to said side edges in said back waist region of said absorbent article, wherein said front panel and said back panel are connected together-along a-side seam which extends between said waist opening and said leg opening to provide said pant-like, disposable absorbent article.

7. The pant-like disposable absorbent article according to claim 1 wherein said side panels are an extensible material.

8. The pant-like disposable absorbent article according to claim 7 wherein said extensible side panels are a neck bonded laminate material.

9. The pant-like disposable absorbent article according to claim 1 wherein said folded fastener includes an active fastening area which remains covered until said folded fastener is unfolded for use.

10. The pant-like disposable absorbent article according to claim 1 wherein said folded fastener is a z-fold fastener which includes a first fold, a second fold located laterally outboard from said first fold, and an active fastening area located laterally outboard from said second fold, and wherein said z-fold fastener is folded upon itself at said first and second folds to provide a z-folded configuration.

11. The pant-like disposable absorbent article according to claim 1 wherein said folded fastener is a j-fold fastener which includes a single fold and an active fastening area located laterally outboard from said single fold, and wherein said j-fold fastener is folded upon itself at said single fold to provide a j-folded configuration.

12. The pant-like disposable absorbent article according to claim 10 wherein said z-fold fastener is located within the releasable joint.

13. The pant-like disposable absorbent article according to claim 11 wherein said j-fold fastener is located within the releasable joint.

14. The pant-like disposable absorbent article according to claim 1 wherein said releasable joint is provided by a combination of permanent bonds and a line of perforations made in said longitudinal direction from said waist opening to said leg opening adjacent said permanent bonds.

15. The pant-like disposable absorbent article according to claim 1 wherein said releasable joint defines a releasable joint length in said longitudinal direction and said folded fastener defines a folded fastener length in said longitudinal direction, wherein said releasable joint length is greater than said folded fastener length.

16. The pant-like disposable absorbent article according to claim 15 wherein said folded fastener length is from about 10 percent to about 80 percent of said releasable joint length.

17. The pant-like disposable absorbent article according to claim 1 and further comprising a second folded fastener located adjacent a second releasable joint, wherein said second folded fastener and said second releasable joint are located on said side panel opposite said at least one side panel, and wherein said first and second folded fasteners are configured to be unfolded and used to refastenably engage said second-side margin of said side panels to said opposite waist region of said absorbent article only after said releasable joints are released.

18. A pant-like, disposable absorbent article which defines a front waist region, a back waist region, a crotch region which extends between and connects said waist regions, a longitudinal direction and a lateral direction, said absorbent article comprising:
   a) an absorbent chassis which defines an absorbent core, an exterior surface, an interior surface opposite said exterior surface, a pair of laterally opposed side edges and a pair of longitudinally opposed waist edges;
   b) a pair of laterally opposed, extensible back panels which are permanently attached to said side edges of said absorbent chassis in said back waist region of said absorbent article;
   c) a pair of laterally opposed, extensible front panels which are releasably attached to said side edges of said absorbent chassis in said front waist region of said absorbent article to provide a pair of releasable joints wherein said front panel and said back panel on each side edge of said absorbent chassis are permanently connected together along a side seam to define a waist opening and a pair of leg openings and provide said pant-like, disposable absorbent article; and
   d) a pair of folded fasteners located adjacent said releasable joints wherein said folded fasteners are held in a folded arrangement and configured to be unfolded and used to refastenably attach said front panels to said front waist region of said absorbent article after said releasable joints are released.

19. The pant-like disposable absorbent article according to claim 18 wherein said folded fasteners include an active fastening area which remains covered until said folded fastener is unfolded for use.

20. The pant-like disposable absorbent article according to claim 18 wherein said folded fasteners are hook and loop type fasteners.

21. The pant-like disposable absorbent article according to claim 20 wherein said folded fasteners are configured to directly, refastenably engage said exterior surface of said absorbent chassis of said disposable absorbent article.

22. The pant-like disposable absorbent article according to claim 20 and further comprising at least one attachment panel which is located on said exterior surface of said absorbent chassis wherein said folded fasteners are configured to refastenably engage said attachment panel.

23. The pant-like disposable absorbent article according to claim 18 wherein said extensible front and back panels are a neck bonded laminate material.

24. The pant-like disposable absorbent article according to claim 18 wherein said releasable joints are provided by ultrasonic bonds.

25. The pant-like disposable absorbent article according to claim 18 wherein said releasable joints are provided by a combination of permanent bonds and a line of perforations made in said longitudinal direction from said waist opening to said leg opening adjacent said permanent bonds.

26. The pant-like disposable absorbent article according to claim 18 wherein said folded fasteners include an extensible panel.

27. The pant-like disposable absorbent article according to claim 18 wherein said folded fasteners are maintained in said folded arrangement by passive ultrasonic bonds.

28. The pant-like disposable absorbent article according to claim 18 wherein said folded fasteners are permanently attached to said exterior surface of said absorbent chassis adjacent said releasable joints.

29. The pant-like disposable absorbent article according to claim 18 wherein said folded fasteners are located within said releasable joints.

30. The pant-like disposable absorbent article according to claim 29 wherein said folded fasteners include an active fastening area that assists in maintaining said releasable joints intact until said releasable joints are released.

31. The pant-like disposable absorbent article according to claim 18 wherein said folded fasteners are z-fold fasteners which include a first fold, a second fold located laterally outboard from said first fold, and an active fastening area located laterally outboard from said second fold, and wherein said z-fold fasteners are folded upon themselves at said first and second folds to provide said folded fasteners in a z-folded configuration.

32. The pant-like disposable absorbent article according to claim 18 wherein said folded fasteners are j-fold fasteners which include a single fold and an active fastening area located laterally outboard from said single fold, and wherein said j-fold fasteners are folded upon themselves at said single fold to provide said folded fasteners in a j-folded configuration.

33. The pant-like disposable absorbent article according to claim 32 wherein a portion of said front side panels are folded inward at said releasable joint to provide a folded portion of said front side panels that provides said folded fasteners in said j-folded configuration and said releasable joints.

34. The pant-like disposable absorbent article according to claim 31 wherein said z-fold fasteners are located within said releasable joints and further include a front side and a back side opposite said front side, said active fastening area being located on said front side, and wherein said front sides of said z-fold fasteners are folded upon themselves at said first fold and said back sides of said z-fold fasteners are folded upon themselves at said second fold to provide said folded fasteners in said z-folded configuration in which said active fastening areas are in position to assist in providing said releasable joints.

35. The pant-like disposable absorbent article according to claim 18 wherein said releasable joint defines a releasable joint length in said longitudinal direction and said folded fastener defines a folded fastener length in said longitudinal direction, wherein said releasable joint length is greater than said folded fastener length.

36. The pant-like disposable absorbent article according to claim 35 wherein said folded fastener length is from about 10 percent to about 80 percent of said releasable joint length.

37. A pant-like, disposable absorbent article which defines a front waist region, a back waist region, a crotch region which extends between and connects said waist regions, a longitudinal direction and a lateral direction, said absorbent article comprising:

a) an absorbent chassis which defines an absorbent core, an exterior surface, an interior surface opposite said exterior surface, a pair of laterally opposed side edges and a pair of longitudinally opposed waist edges;

b) a pair of laterally opposed, extensible back panels which are permanently attached to said side edges of said absorbent chassis in said back waist region of said absorbent chassis;

c) a pair of laterally opposed, extensible front panels which are permanently attached to said side edges of said absorbent chassis in said front waist region of said absorbent article wherein said front panel and said back panel on each side edge of said absorbent chassis are refastenably connected together along a side seam to provide a pair of releasable joints and to define a waist opening and a pair of leg openings and provide said pant-like, disposable absorbent article; and d) a pair of folded fasteners located adjacent said releasable joints wherein said folded fasteners are held in a folded arrangement and configured to be unfolded and used to refastenably engage said back panels to said front waist region of said absorbent article after said releasable joints are released.

38. The pant-like disposable absorbent article according to claim 37 wherein said folded fasteners include an active fastening area which remains covered until said folded fasteners are unfolded for use.

39. The pant-like disposable absorbent article according to claim 37 wherein said folded fasteners are hook and loop type fasteners.

40. The pant-like disposable absorbent article according to claim 39 wherein said folded fasteners are configured to directly, refastenably engage said exterior surface of said absorbent chassis of said disposable absorbent article.

41. The pant-like disposable absorbent article according to claim 39 and further comprising at least one attachment panel which is located on said exterior surface of said absorbent chassis wherein said folded fasteners are configured to refastenably engage said attachment panel.

42. The pant-like disposable absorbent article according to claim 37 wherein said extensible front and back panels are a neck bonded laminate material.

43. The pant-like disposable absorbent article according to claim 37 wherein said releasable joints are provided by ultrasonic bonds.

44. The pant-like disposable absorbent article according to claim 37 wherein said releasable joints are provided by a combination of permanent bonds and a line of perforations made in said longitudinal direction from said waist opening to said leg opening adjacent said permanent bonds.

45. The pant-like disposable absorbent article according to claim 37 wherein said folded fasteners include an extensible panel.

46. The pant-like disposable absorbent article according to claim 37 wherein said folded fasteners are maintained in a folded configuration by passive ultrasonic bonds.

47. The pant-like disposable absorbent article according to claim 37 wherein said folded fasteners are permanently attached to said exterior surface of said absorbent chassis adjacent said releasable joints.

48. The pant-like disposable absorbent article according to claim 37 wherein said folded fasteners are located within said releasable joints.

49. The pant-like disposable absorbent article according to claim 48 wherein said folded fasteners include an active fastening area that assists in maintaining said releasable joints intact until said releasable joints are released.

50. The pant-like disposable absorbent article according to claim 37 wherein said folded fasteners are z-fold fasteners which include a first fold, a second fold located laterally outboard from said first fold, and an active fastening area located laterally outboard from said second fold, and wherein said z-fold fasteners are folded upon themselves at said first and second folds to provide said folded fasteners in a z-folded configuration.

51. The pant-like disposable absorbent article according to claim 37 wherein said folded fasteners are j-fold fasteners which include a single fold and an active fastening area located laterally outboard from said single fold, and wherein said j-fold fasteners are folded upon themselves at said single fold to provide said folded fasteners in a j-folded configuration.

52. The pant-like disposable absorbent article according to claim 51 wherein a portion of said back side panels are folded longitudinally inward at said releasable joint to provide a folded portion of said back side panels that provides said folded fasteners in said j-folded configuration and said releasable joints.

53. The pant-like disposable absorbent article according to claim 50 wherein said z-fold fasteners are located within said releasable joints and further include a front side and a back side opposite said front side, said active fastening area being located on said front side, and wherein said front sides of said z-fold fasteners are folded upon themselves at said first fold and said back sides of said z-fold fasteners are folded upon themselves at said second fold to provide said folded fasteners in said z-folded configuration in which said active fastening areas are in position to assist in providing said releasable joints.

54. The pant-like disposable absorbent article according to claim 37 wherein said releasable joint defines a releasable joint length in said longitudinal direction and said folded fastener defines a folded fastener length in said longitudinal direction, wherein said releasable joint length is greater than said folded fastener length.

55. The pant-like disposable absorbent article according to claim 54 wherein said folded fastener length is from about 10 percent to about 80 percent of said releasable joint length.

56. A pant-like, disposable absorbent article which defines a front waist region, a back waist region, a crotch region which extends between and connects said waist regions, a longitudinal direction and a lateral direction, said absorbent article comprising:

a) an absorbent chassis which defines an absorbent core, an exterior surface, an interior surface opposite said exterior surface, a pair of laterally opposed side edges and a pair of longitudinally opposed waist edges;

b) a pair of laterally opposed, extensible back panels which are permanently attached to said side edges of said absorbent chassis in said back waist region of said absorbent chassis;

c) a pair of laterally opposed, extensible front panels which are permanently attached to said side edges of said absorbent chassis in said front waist region of said absorbent article wherein said front panel and said back panel on each side edge of said absorbent chassis are refastenably connected together along a side seam to provide a pair of releasable joints and to define a waist opening and a pair of leg openings and provide said pant-like, disposable absorbent article; and d) a pair of folded fasteners defining an inboard edge attached to said article and an outboard edge wherein said inboard edge defines a length in said longitudinal direction which is greater than a length of said outboard edge in said longitudinal direction, and wherein said folded fasteners are held in a folded arrangement and configured to be unfolded and used to refastenably engage said back panels to said front waist region of said absorbent article after said releasable joints are released.

57. The pant-like disposable absorbent article according to claim 56 wherein said folded fasteners further define an upper lateral edge and a lower lateral edge, and wherein said lower lateral edge defines a curvilinear shape.

58. The pant-like disposable absorbent article according to claim 56 wherein said folded fasteners include an active fastening area which remains covered until said folded fasteners are unfolded for use.

59. The pant-like disposable absorbent article according to claim 56 wherein said folded fasteners are hook and loop type fasteners.

60. The pant-like disposable absorbent article according to claim 56 wherein said length of said outboard edge is from about 10 percent to about 80 percent of said length of said inboard edge.

* * * * *